(12) United States Patent
Pimanda et al.

(10) Patent No.: US 9,982,232 B2
(45) Date of Patent: May 29, 2018

(54) METHODS OF GENERATING CELLS WITH MULTILINEAGE POTENTIAL

(71) Applicant: NEWSOUTH INNOVATIONS PTY LIMITED, Sydney, New South Wales (AU)

(72) Inventors: John Pimanda, Woollahra (AU); Vashe Chandrakanthan, Coogee (AU)

(73) Assignees: John Pimanda, Woollahra (AU); Vashe Chandrakanthan, Coogee (AU)

( * ) Notice: Subject to any disclaimer, the term of this patent is extended or adjusted under 35 U.S.C. 154(b) by 0 days. days.

(21) Appl. No.: 14/652,552

(22) PCT Filed: Dec. 17, 2013

(86) PCT No.: PCT/AU2013/001476
§ 371 (c)(1),
(2) Date: Jun. 16, 2015

(87) PCT Pub. No.: WO2014/094043
PCT Pub. Date: Jun. 26, 2014

(65) Prior Publication Data
US 2016/0145575 A1    May 26, 2016

(30) Foreign Application Priority Data

Dec. 17, 2012  (AU) ................................ 2012905513

(51) Int. Cl.
| | | |
|---|---|---|
| *C12N 5/074* | (2010.01) | |
| *C12N 5/0775* | (2010.01) | |
| *A61K 35/32* | (2015.01) | |
| *A61K 35/33* | (2015.01) | |
| *A61K 35/35* | (2015.01) | |
| *A61K 31/706* | (2006.01) | |
| *A61L 27/16* | (2006.01) | |
| *A61L 27/38* | (2006.01) | |
| *A61L 27/52* | (2006.01) | |
| *A61K 35/28* | (2015.01) | |
| *A61K 38/18* | (2006.01) | |

(52) U.S. Cl.
CPC .......... *C12N 5/0662* (2013.01); *A61K 31/706* (2013.01); *A61K 35/28* (2013.01); *A61K 35/32* (2013.01); *A61K 35/33* (2013.01); *A61K 35/35* (2013.01); *A61K 38/1858* (2013.01); *A61L 27/16* (2013.01); *A61L 27/3804* (2013.01); *A61L 27/3834* (2013.01); *A61L 27/3843* (2013.01); *A61L 27/3847* (2013.01); *A61L 27/3852* (2013.01); *A61L 27/3895* (2013.01); *A61L 27/52* (2013.01); *A61L 2300/414* (2013.01); *A61L 2430/02* (2013.01); *C12N 2500/40* (2013.01); *C12N 2501/06* (2013.01); *C12N 2501/135* (2013.01); *C12N 2503/02* (2013.01); *C12N 2506/13* (2013.01)

(58) Field of Classification Search
CPC ............................ C12N 5/0662; C12N 5/0607
See application file for complete search history.

(56) References Cited

U.S. PATENT DOCUMENTS

| | | | |
|---|---|---|---|
| 2005/0181502 A1* | 8/2005 | Furcht .................. | C12N 5/0607 435/354 |
| 2006/0084172 A1 | 4/2006 | Muller et al. | |
| 2006/0182724 A1* | 8/2006 | Riordan ................. | A61K 8/982 424/93.7 |
| 2007/0020759 A1 | 1/2007 | Sayre et al. | |
| 2008/0050347 A1* | 2/2008 | Ichim ..................... | A61K 35/12 424/93.7 |
| 2008/0268054 A1* | 10/2008 | Bell ...................... | A61K 35/545 424/484 |
| 2012/0220034 A1* | 8/2012 | Ahlfors ................ | C12N 5/0618 435/375 |

OTHER PUBLICATIONS

Jopling et al, "Dedifferentiation, transdifferentiation and reprogramming: three routes to regeneration" Nature Reviews, 2011, vol. 12, pp. 79-89.*
Takahashi et al "Induction of Pluripotent stem cells from mouse embryonic and adult fibroblast cultures by defined factors" Cell, 2006, vol. 126, pp. 663-676.*
Ullah et al, "Transdifferentiation of mesenchymal stem cells-derived adipogenic-differentiated cells into osteogenic- or chondrogenic-differenaited cells proceeds via dedifferentiation and have a correlation with cell cycle arresting and driving genes" Differentiation, 2013, vol. 85, pp. 78-90.*
Barberi et al.; *Derivation of Multipotent Mesenchymal Precursors from Human Embryonic Stem Cells*; PLoS Medicine; vol. 2; Issue 6; pp. 0554-0560; 2005.
Banas et al.; *Adipose Tissue-Derived Mesenchymal Stem Cells as a Source of Human Hepatocytes*; Hepatology 46(1); pp. 219-228; 2007.
Harris et al.; *Transformation of Human Mesenchymal Cells and Skin Fibroblasts into Hematopoietic Cells*; PLoS ONE; vol. 6; issue 6; pp. 1-16; 2011.
Chandrakanthan et al.; *Reprogramming Lineage Committed Cells into MSC-like Cells and Tissue Repair Potential Using Pdgf-AF and Azacitidine*; 6th Annual Meeting of the Australasian Society for Stem Cell Research; Oct. 27-29, 2013 Abstract 8528; pp. 1-3.
International Search Report for PCT/AU2013/001476, dated Feb. 10, 2014.

* cited by examiner

*Primary Examiner* — Allison M Fox
(74) *Attorney, Agent, or Firm* — Wenderoth, Lind & Ponack, L.L.P.

(57) ABSTRACT

The present invention relates to methods for generating mammalian multilineage-potential cells, including mesenchymal stem cells, comprising contacting mammalian somatic cells exhibiting a mature phenotype with PDGF-AB or functional derivative, fragment or mimetic thereof and Azacitidine or functional derivative or analog thereof for a time and under conditions sufficient to induce the transition of the somatic cells to cells exhibiting multilineage differentiative potential. Also provided are uses of said multilineage-potential cells, such as in promoting tissue repair and regeneration.

10 Claims, 9 Drawing Sheets

METHODS OF GENERATING CELLS WITH MULTILINEAGE POTENTIAL

FIELD OF THE INVENTION

The present invention relates generally to methods of generating cells exhibiting multilineage potential and to cells generated thereby. More particularly, the present invention is directed to methods of generating mammalian stem cells exhibiting mesenchymal potential and to cells generated thereby. The methods of the present invention facilitate the generation of cells of multilineage potential in either the in vitro or in vivo environments. This finding has now facilitated the design of means for reliably and efficiently generating populations of multilineage potential cells, such as stem cells, for use in a wide variety of clinical and research settings. These uses include, inter alia, the in vitro and in vivo generation of mesenchymal stem cells, the repair and regeneration of tissue and the therapeutic or prophylactic treatment of a range of conditions either via the administration of the multilineage potential cells of the invention, or more fully differentiated cellular populations derived therefrom, or via the in vivo stimulation of cellular differentiation. Also facilitated is the design of in vitro based screening systems for testing the therapeutic impact and/or toxicity of potential treatment or culture regimes to which these cells may be exposed.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The regenerative potential of most terminally differentiated tissues is limited and diminishes with age. As a consequence, disabilities from common ailments such as bone fractures and joint degeneration are compounded with increasing age. Beyond the personal cost to the individual and their families, the accrued financial cost to the health system and the economy is also significant. Harvesting and expanding stem/progenitor cells for cell based therapy to treat common disorders in bone and cartilage is both cumbersome and impractical for large scale application and runs the risk of inappropriate tissue and scar formation at the graft site. Exogenous therapies such as BMP2 are expensive, are required in high dose and can give rise to ectopic bone formation.

Although activating resident stem/progenitor cells to help repair tissues may be an attractive option, low starting numbers of these cells is a limiting factor. Most structural tissues do not have a leading front of precursors that are ready to replace senescent, damaged or lost cells, even if they have a reserve of adult tissue resident stem cells. Reprogramming differentiated cells, triggering de-differentiation, replication and proliferation, is an alternate strategy provided this expanded pool of progenitors then follows resident cues to regenerate the cognate tissue.

The ability to regenerate large sections of the body plan is widespread in metazoan phylogeny but in adult vertebrates, limb regeneration is limited to urodele amphibians (salamanders). Limb regeneration in urodeles is dependent on plasticity of differentiated cells where mesenchymal tissues such as cartilage, muscle and connective tissue underlying the wound epidermis, lose their differentiated characteristics and adopt a blastemal cell state. The blastema is essentially a zone of mesenchymal cells that proliferate, differentiate and regenerate the limb according to the pre-determined body plan. It would be an important advance, and a development of significant clinical potential, if the regenerative response in salamanders could be replicated in mammalian cells, whereby differentiated tissues lose their identity and adopt a blastemal state, and contribute to tissue repair by regeneration in response to injury rather than by scarring.

In work leading up to the present invention, it has been determined that mesenchymal cell expansion does not necessarily need to occur by virtue of asymmetric stem cell division to provide both stem cell renewal and linear differentiation of the relevant daughter cell along the mesenchymal lineage through to terminal differentiation. Rather, expansion can be achieved by virtue of the transition of a mature somatic cell to a cell with multilineage potential, in particular a mesenchymal stem cell. Described herein is a novel means for reliably and efficiently generating, from differentiated cells, cells which exhibit multilineage potential, either in vitro or in vivo, thereby providing a valuable mechanism by which mesenchymal stem cell populations and/or somatic cells differentiated therefrom can be made available for a variety of research and clinical applications such as those requiring tissue repair and/or regeneration.

SUMMARY OF THE INVENTION

A first aspect of the present invention provides a method of generating a mammalian multilineage-potential cell, said method comprising contacting a mammalian somatic cell exhibiting a mature phenotype with PDGF-AB or functional derivative, fragment or mimetic thereof and Azacitidine or functional derivative or analogue thereof for a time and under conditions sufficient to induce the transition of said somatic cell to a cell exhibiting multilineage differentiative potential.

The mammalian somatic cell exhibiting a mature phenotype may be a differentiated cell. In a particular embodiment the mammalian somatic cell exhibiting a mature phenotype is a mesenchyme-derived somatic cell.

In an embodiment the mammalian somatic cell exhibiting a mature phenotype is selected from a fibroblast, adipocyte, chondrocyte, osteoblast and osteocyte.

The multilineage-potential cell may be a mesenchymal stem cell. The mesenchymal stem cell may be a pluripotent or multipotent stem cell.

In an embodiment the cell may be contacted for a first period of time with the PDGF-AB or functional derivative, fragment or mimetic thereof and Azacitidine or functional derivative or analogue thereof, and subsequently for a second period of time with the PDGF-AB or functional derivative, fragment or mimetic thereof in the absence of the Azacitidine or functional derivative or analogue thereof.

The first period of time may be, for example, between 12 to 72 hours. In a particular exemplary embodiment the first period is 48 hours.

The second period of time may be, for example, between 7 to 12 days. In a particular exemplary embodiment the second period is 10 days.

In a second aspect there is provided a method of facilitating the generation of a mammalian MSC-derived cell, said method comprising:
(i) contacting a somatic cell exhibiting a mature phenotype with PDGF-AB or functional derivative, fragment or mimetic thereof and Azacitidine or functional derivative or analogue thereof for a time and under conditions sufficient to induce the transition of said somatic cell to a cell exhibiting multilineage differentiative potential; and optionally (ii) contacting the cell produced in step (i) with a stimulus to direct the differentiation of said cell to a mesenchymal phenotype.

The mammalian somatic cell exhibiting a mature phenotype may be a differentiated cell. In a particular embodiment the mammalian somatic cell exhibiting a mature phenotype is a mesenchyme-derived somatic cell.

In an embodiment the mammalian somatic cell exhibiting a mature phenotype is selected from a fibroblast, adipocyte, chondrocyte, osteoblast and osteocyte.

The multilineage-potential cell may be a mesenchymal stem cell. The mesenchymal stem cell may be a pluripotent or multipotent stem cell. The MSC-derived cell may be a partially differentiated or fully differentiated cell.

A third aspect of the invention provides a method for promoting or inducing tissue repair or regeneration, said method comprising administering to a mammal in need thereof:

(i) an effective number of multilineage-potential cells generated according to the first aspect, or partially or fully differentiated MSC-derived cells generated according to the second aspect; or (ii) an effective amount of PDGF-AB, functional derivative, fragment or mimetic thereof and Azacitidine or functional derivative or analogue thereof, or other stimulus, suitable for effecting the in vivo generation of the cells of (i) in accordance with the methods hereinbefore defined.

In an exemplary embodiment, the tissue is connective tissue. The tissue may be selected from bone, cartilage, smooth muscle, tendon, ligament, stroma, marrow, dermis and fat.

A fourth aspect of the invention provides a method of therapeutically and/or prophylactically treating a condition in a mammal, said method comprising administering to said mammal:

(i) an effective number of multilineage-potential cells generated according to the first aspect, or partially or fully differentiated MSC-derived cells generated according to the second aspect; or (ii) an effective amount of PDGF-AB or functional derivative, fragment or mimetic thereof and Azacitidine or functional derivative or analogue thereof, or other stimulus, suitable for effecting the in vivo generation of the cells of (i) in accordance with the methods hereinbefore defined.

In an exemplary embodiment of the third and fourth aspects, the PDGF-AB or functional derivative, fragment or mimetic thereof and Azacitidine or functional derivative or analogue thereof are contacted with tissue ex vivo and introduced into a subject in need thereof. The PDGF-AB or functional derivative, fragment or mimetic thereof and Azacitidine or functional derivative or analogue thereof and tissue may be cultured together prior to introduction into the subject. The tissue may be autogeneic or allogeneic.

In an alternate exemplary embodiment of the third and fourth aspects, one or both of the PDGF-AB or functional derivative, fragment or mimetic thereof and Azacitidine or functional derivative or analogue thereof are delivered to a subject in need thereof in a polymeric carrier. The polymeric carrier may comprise a biodegradable or non-biodegradable gel. The gel may be a hydrogel. The polymeric carrier may provide for sustained or delayed release of one or both of the PDGF-AB or functional derivative, fragment or mimetic thereof and Azacitidine or functional derivative or analogue thereof.

In an alternate exemplary embodiment of the third and fourth aspects, one or both of the PDGF-AB or functional derivative, fragment or mimetic thereof and Azacitidine or functional derivative or analogue thereof are coated onto an implantable device and the coated device introduced into a subject in need thereof. The implantable device may be an orthopaedic implant.

A further aspect of the invention provides the use of a population of multilineage-potential cells generated according to the first aspect, or partially or fully differentiated MSC-derived cells generated according to the second aspect, in the manufacture of a medicament for promoting tissue repair and/or regeneration, or treating a condition in a mammal.

A further aspect of the present invention provides an isolated population of multilineage-potential cells generated according to the first aspect, or partially or fully differentiated MSC-derived cells generated according to the second aspect.

A further aspect of the present invention provides a method of assessing the effect of a treatment or culture regime on the phenotypic or functional state of a multilineage-potential cell or MSC-derived cell, said method comprising subjecting said multilineage-potential cells generated according to the first aspect, or partially or fully differentiated MSC-derived cells generated according to the second aspect, to said treatment regime and screening for an altered functional or phenotypic state.

BRIEF DESCRIPTION OF THE DRAWINGS

Embodiments of the present invention are described herein, by way of non-limiting examples only, with reference to the following drawings.

DETAILED DESCRIPTION OF THE INVENTION

Figure 1:
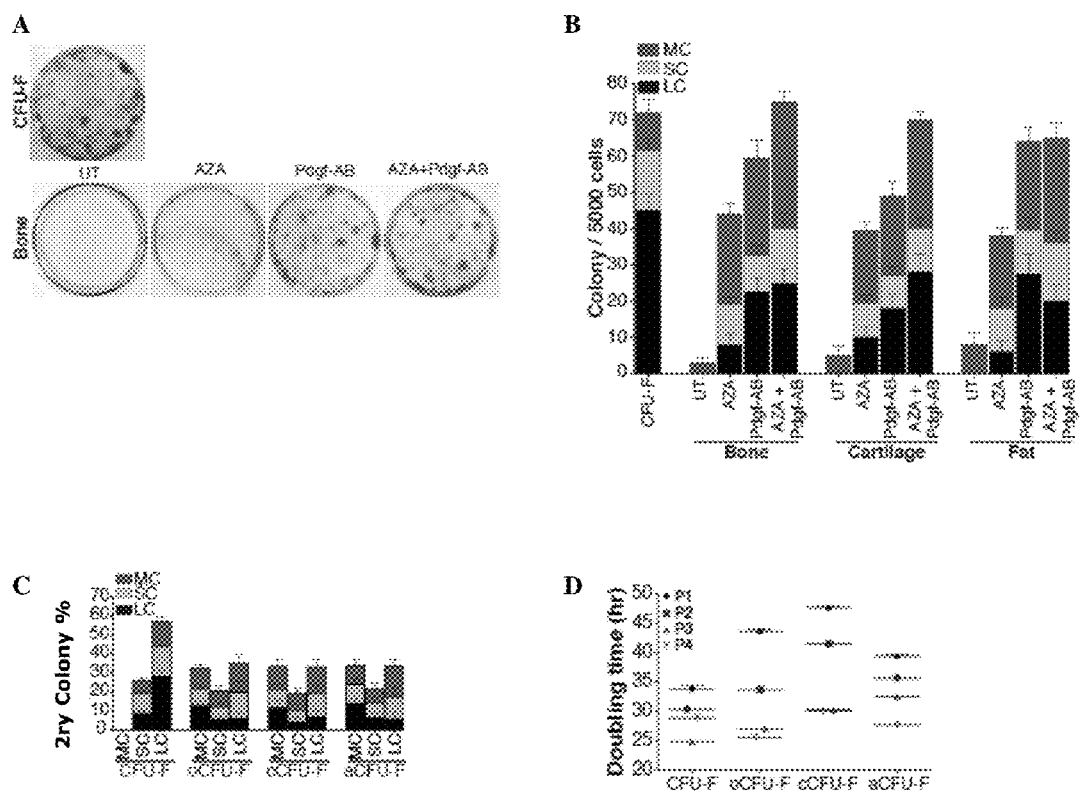
FIG. 1: PDGF-AB in combination with AZA reprograms in vitro derived bone, cartilage and fat cells into multipotent MSC-like cells. (A) Crystal violet stained CFU-F colonies from bone cells maintained in MSC medium supplemented with PDGF-AB or AZA alone and in combination. (B) Colony number (based on size) for CFU-F colonies from bone, cartilage and fat cells maintained in MSC medium supplemented with PDGF-AB or AZA alone and in combination. (C) Secondary colony forming potential of re-plated single cells from micro, small and large colonies. (D) Cell doubling times of passage 1-4 oCFU-F, cCFU-F and aCFU-Fs derived from bone, cartilage and fat cells treated with the combination of PDGF-AB and AZA. Freshly isolated bone marrow CFU-Fs (passages 1-4) are shown as a control. (E) Flowcytometry profiles of bone marrow derived bone, cartilage and fat cells maintained in MSC medium alone or medium supplemented with PDGF-AB and AZA. The MSC markers, Sca-1, CD90.2, CD105 or CD166 are expressed on oCFU-F, cCFU-F and aCFU-Fs at levels and frequencies comparable with that expressed on freshly isolated CFU-Fs. (F) oCFU-Fs can be differentiated into bone (alizarin red), cartilage (alcian blue) and fat (oil red O). BM; bone marrow, CFU-F; colony forming unit-fibroblast, oCFU-F; cytokine/AZA treated bone cells cultured in MSC medium, cCFU-F; cytokine/AZA treated cartilage cells cultured in MSC medium, aCFU-F; cytokine/AZA treated fat cells cultured in MSC medium, P; passage, UT; untreated. Error bars=SEM between independent experiments.
Figure 1:
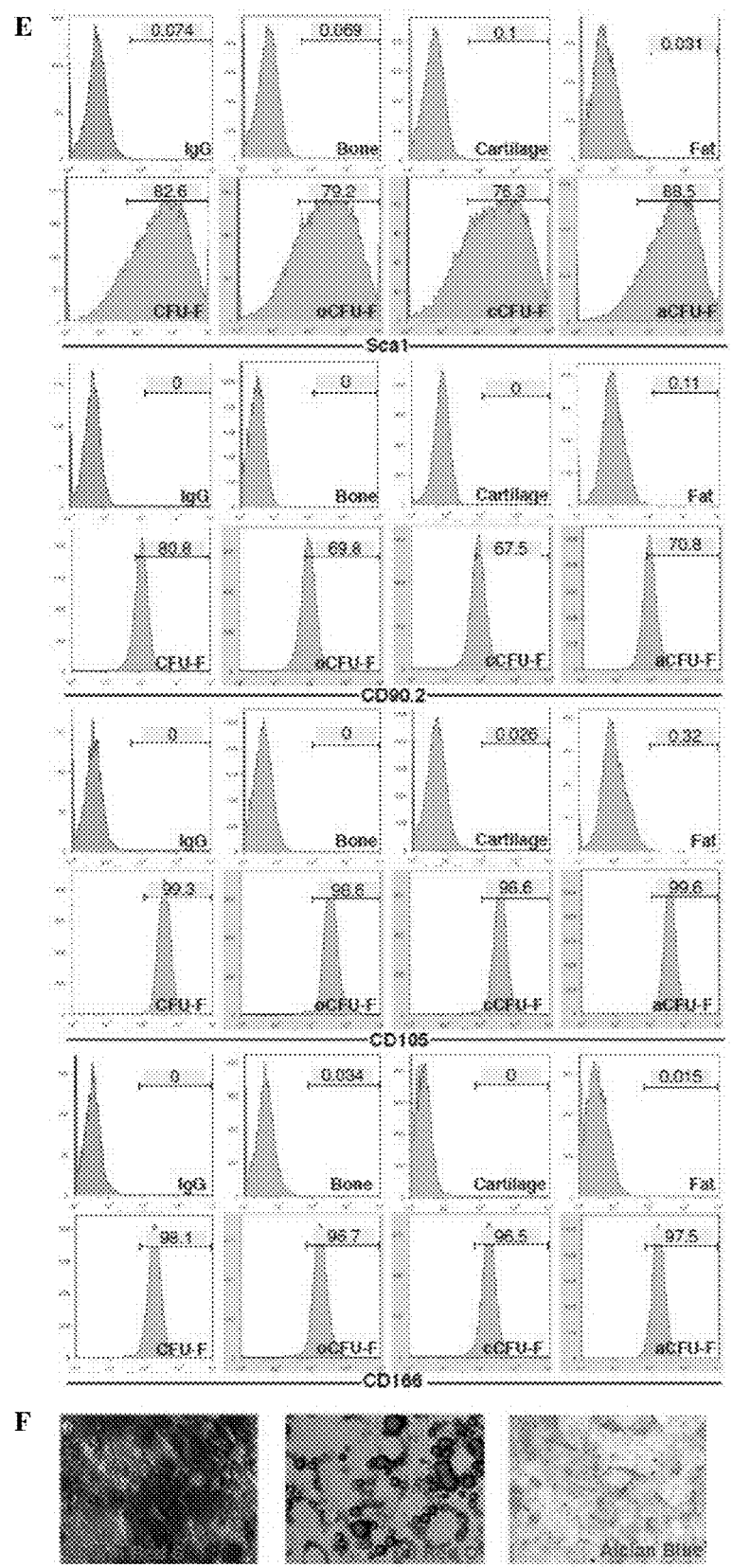

Unless otherwise defined, all technical and scientific terms used herein have the same meaning as commonly understood by one of ordinary skill in the art to which this invention belongs.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The terms "mammal" and "mammalian" as used herein include humans, primates, livestock animals (e.g. horses, cattle, sheep, pigs, donkeys), laboratory test animals (e.g. mice, rats, guinea pigs), companion animals (e.g. dogs, cats) and captive wild animal (e.g. kangaroos, deer, foxes). Typically, the mammal is a human, laboratory test animal, performance animal or companion animal. Even more typically, the mammal is a human.

Reference to "culture" in the context of the present invention should be understood as a reference to both the in vitro and in vivo models of generating the mesenchymal stem cells of the present invention.

As used herein the singular forms of "a", "and" and "the" include plural referents unless the context clearly dictates otherwise.

The present invention is predicated, in part, on the determination described herein that mesenchymal stem cells can be sourced from mature mesenchymal derived somatic cells which are induced to transition to a state of multilineage potential, this being followed by symmetrical division and differentiation under the appropriate stimulus. This finding is of significant importance since it has been a particular difficulty in the art that methods of efficiently inducing stem cell renewal and expansion in vitro have not been realised.

As described and exemplified herein, the present inventors cultured lineage committed cells with a range of growth factors associated with MSC growth with and without AZA to evaluate whether cell proliferation and de-differentiation could be induced. Differentiated somatic cells can be reprogrammed to MSC like cells (iMSC-LCs) with tissue repair potential by Pdgf-AB and AZA. These reprogrammed cells demonstrate serial clonogenicity and long-term self-renewal, multi-lineage differentiation, express surface markers and a transcriptome that resembles but is not identical to that of primary BM-MSCs. They do not form teratomas and demonstrate in vitro and in vivo plasticity, and thus can contribute both to tissue regeneration and repair.

A significant translational benefit of the findings described herein is the promotion of tissue repair using PDGF-AB/AZA. To this end, the present inventors also describe herein transplantation experiments taking long bone fragments from ubiquitous GFP expressing mice to assess their capacity to integrate with host tissues using a posterolateral inter-transverse lumbar fusion mouse model. Whereas untreated bone fragments failed to integrate and fuse, bone fragments treated with PDGF-AB/AZA for 12 days generate new bone and fuse. Moreover, cells from grafted PDGF-AB/AZA treated bone, also contribute to muscle repair, with evidence that they also contribute to the nascent vasculature.

The present invention therefore provides a means for the routine generation of mammalian mesenchymal stem cells, either in vitro or in vivo, based on inducing the transition of a mature mammalian somatic cell to a mesenchymal stem cell phenotype that exhibits multilineage potential. Accordingly, the potential in vivo and in vitro applications of these findings are extremely widespread including, but not limited to, the in vitro generation of mesenchymal stem cell populations, in vivo mobilisation of mesenchymal stem cells, directed differentiation of the subject mesenchymal stem cells either in vitro or in vivo, therapeutic or prophylactic treatment regimes based thereon, repair and/or regeneration of tissue, and the in vitro assessment of the effectiveness and/or toxicity of potential treatment or culture regimes to which the cells of the invention may be exposed.

Accordingly, one aspect of the present invention is directed to a method of generating a mammalian multilineage-potential cell, said method comprising contacting a mammalian somatic cell exhibiting a mature phenotype with PDGF-AB or functional derivative, fragment or mimetic thereof and Azacitidine or functional derivative or analogue thereof for a time and under conditions sufficient to induce the transition of said somatic cell to a cell exhibiting multilineage differentiative potential.

Reference to a "somatic cell exhibiting a mature phenotype" should be understood as a reference to a somatic cell that exhibits one or more of the functional or morphological features of a mature somatic cell. In this regard, it should be understood that any given feature is not necessarily one that is exhibited exclusively by the subject mature somatic cell. However, where a cell does not express a functional or structural feature which is unique to the somatic cell, its characterisation as the subject mature somatic cell may be linked to the expression of two or more such characteristics which, when expressed by a single cell, is characteristic of the subject mature somatic cell. To this end, some cells may exhibit more than one mature phenotype. For example, unactivated B cells that are sufficiently differentiated such that they are receptive to an activation signal, nevertheless undergo a further differentiation event subsequently to activation, this being the transition to a plasma cell state. This latter state is often referred to as a "terminally differentiated" state while the former is commonly known as a "fully differentiated" state. Many other mature cell types similarly demonstrate morphological or functional changes upon activation or exposure to a particular environmental signal. It should be understood that in the context of the present invention, reference to a "mature somatic cell" is intended to encompass cells falling within the scope of either of these states of maturity or differentiation and not merely cells which are terminally differentiated, such as plasma cells.

In one embodiment, the mature somatic cell is a mesenchyme-derived somatic cell.

Accordingly, a further aspect of the invention provides a method of generating a mammalian multilineage-potential cell, said method comprising contacting a mammalian mesenchyme-derived somatic cell exhibiting a mature phenotype with PDGF-AB or functional derivative, fragment or mimetic thereof and Azacitidine or functional derivative or analogue thereof for a time and under conditions sufficient to induce the transition of said somatic cell to a cell exhibiting multilineage differentiative potential.

Reference to a "mesenchyme-derived" somatic cell should be understood as a reference to a cell that is derived from the mesenchyme. Without limiting the present invention to any one theory or mode of action, mesenchyme (also known as mesenchymal connective tissue) is a type of undifferentiated loose connective tissue that is derived mostly from the mesoderm, although it can sometimes be derived from other germ layers. "Connective tissue" is therefore a generalised term for mesodermally derived tissue which may be more or less specialised. For example, cartilage and bone are forms of specialised connective tissue. Other forms of less specialised connective tissue include the tissues which are rich in extracellular matrix and surround other more highly ordered tissues and organs. Connective tissue therefore comprises many cell types which exhibit a variety of functions. Connective tissue cells, of which mesenchymal-derived cells form a proportion, may originate locally and remain in the connective tissue or they may originate elsewhere and remain only transiently in the connective tissue. Mesenchymal cells are able to develop into the tissues of the lymphatic and circulatory systems as well as connective tissues throughout the body such as bone, cartilage, smooth muscle, tendon, ligament, stroma, marrow, dermis and fat. In another embodiment, said mesenchyme-derived somatic cell is a fibroblast, adipocyte, chondrocyte osteocyte, osteoblast, pericyte or endothelial muscle cell.

Also provided herein is a method of generating a mammalian multilineage-potential cell, said method comprising contacting a mammalian fibroblast, adipocyte, chondrocyte, osteoblast and/or osteocyte with PDGF-AB or functional derivative, fragment or mimetic thereof and Azacitidine or functional derivative or analogue thereof for a time and under conditions sufficient to induce the transition of the somatic cell to a cell exhibiting multilineage differentiative potential.

As detailed hereinbefore, it has been determined that a mature somatic cell can be induced to transition into a state of multilineage differentiation potential. Accordingly, reference to a cell exhibiting "multilineage differentiation potential", "multilineage differentiative potential" or "multilineage potential" should be understood as a reference to a cell which exhibits the potentiality to develop along more than one somatic differentiative path. For example, the cell may be capable of generating a range of somatic cell types, such cells usually being referred to as pluripotent or multipotent. These cells exhibit commitment to a more limited range of lineages than a totipotent cell, the latter being a cell which can develop in any of the differentiation directions inherently possible including all the somatic lineages and the gametes. Without limiting the present invention to any one theory or mode of action, to the extent that a stem cell is derived from post-natal tissue, it is also often referred to as an "adult stem cell". Many cells that are classically termed "progenitor" cells or "precursor" cells may also fall within the scope of the definition of "multilineage differentiation potential" on the basis that, under appropriate stimulatory conditions, they can give rise to cells of more than one somatic lineage. To the extent that reference to "stem cell" is made herein in terms of the cells generated by methods of the invention, this should be understood as a reference to a cell exhibiting multilineage differentiative potential as herein defined.

In one embodiment said mesenchyme-derived somatic cells can be induced to transition to mesenchymal stem cells and thereafter along any one of the mesenchymal lineages. Without limiting the present invention to any one theory or mode of action, mesenchymal stem cells are examples of a committed stem cell (also often referred to as a multipotential stem cell) which can differentiate down a limited number of somatic pathways. Mesenchymal stem cell can be directed to differentiate to connective tissues such as bone, cartilage, smooth muscle, tendon, ligament, stroma, marrow, dermis and fat.

Accordingly, one particular aspect of the present invention is directed to a method of generating a mesenchymal stem cell, said method comprising contacting a mammalian mesenchyme-derived somatic cell with PDGF-AB or functional derivative, fragment or mimetic thereof and Azacitidine or functional derivative or analogue thereof for a time and under conditions sufficient to induce the transition of said somatic cell to a mesenchymal stem cell.

Mesenchymal stem cells are naturally very rare, existing at an estimated frequency of 1 in 100,000 bone marrow cells. Mature, fully differentiated mesenchymal-derived cells are the result of a step-wise maturation process termed mesogenesis. In addition to the localisations specified above, mesenchymal stem cells are also found in a variety of other tissues including, but not limited to dental pulp and uterus. Reference to a "mesenchymal stem cell" should therefore be understood as a reference to any cell which exhibits the potentiality to develop to a cell exhibiting one or more of the functional or phenotypic characteristics which are exhibited by a mesenchymal or mesenchymal-derived cell but not a non-mesenchymal-derived cell such as an endodermal derived cell type. Mesenchymal stem cells are also alternatively known as "stromal stem cells", "adult stem cells", "adiposed derived stem cells", "lipoaspirate derived stem cells" and "post natal stem cells". Reference to "functional" feature should be understood as a reference to any cell which is committed to differentiating to a mesenchymal cell (e.g. a mesodermal cell which is committed to differentiating to a mesenchymal stem cell) or a mesenchymal stem cell which is committed to or exhibits the ability to differentiate along any one or more of the mesenchymal cell derived lineages, such as those which comprise the dermis, bone, cartilage or circulatory system, for example, endothelial cells, smooth muscle cells, pericytes and cardiomyocytes. In this regard, it should be understood that any given functional or phenotypic feature is not necessarily one which is exclusively exhibited by a mesenchymal stem cell. However, where a cell does not express a functional or phenotypic feature which is unique to a mesenchymal stem cell, its characterisation as a mesenchymal stem cell may be linked to the expression of two or more such characteristics which, when expressed by a single cell, are characteristic of a mesenchymal stem cell.

The mesenchymal stem cells that are generated in accordance with methods of the invention are defined as cells which are not terminally differentiated. Accordingly, although it is a preferred embodiment that the subject cells are capable of differentiating along any mesenchymal lineage (i.e. multipotent mesenchymal cells), they may also correspond to cells which are capable of differentiating along just some of the mesenchymal lineages. Alternatively, the cell may be committed to differentiating along one specific lineage but nevertheless corresponds to a precursor cell in that it is not terminally differentiated. Accordingly, the subject mesenchymal stem cell may be a progenitor mesenchymal cell, precursor mesenchymal cell, pluripotent mesenchymal cell, multipotent mesenchymal cell or a de-differentiated, mesenchymal cell. Typically, the subject mesenchymal stem cell is a pluripotent or multipotent mesenchymal cell.

Accordingly, also provided herein is a method of generating a mammalian multilineage-potential cell, said method comprising contacting a mammalian mesenchyme-derived somatic cell with PDGF-AB or functional derivative, fragment or mimetic thereof and Azacitidine or functional derivative or analogue thereof for a time and under conditions sufficient to induce the transition of said somatic cell to a pluripotent or multipotent mesenchymal stem cell.

In particular embodiments, said mesenchyme-derived somatic cell is a fibroblast, adipocyte, chondrocyte or osteocyte.

Reference to inducing the "transition" of a somatic cell to a multilineage potential phenotype should be understood as a reference to inducing the genetic, morphologic and/or functional changes which are required to change a somatic phenotype to a multilineage potential phenotype of the type defined herein. Without limiting the present invention in any way, it is thought that the subject somatic cell may require only certain epigenetic cues to change its phenotype in this way. Those epigenetic cues may include DNA demethylation, chromatin remodelling (e.g. histone modification including histone acetylation/deacetylation; histone methylation/demethylation, histone phosphorylation, histone ubiquilation, histone sumoylation), modification of cis-regulatory elements (e.g. promoters, enhancers, insulators) or RNA interference.

In terms of inducing the transition of a mature somatic cell to a stem cell, this can be achieved either in vitro, such as in the context of small scale in vitro tissue culture or large scale bioreactor production, or in an in vivo microenvironment, such as where an appropriate signal is provided to a mature somatic cell, in situ.

As detailed hereinbefore, it has been determined that the transition of a somatic cell to a cell of multilineage potential is achieved by contacting the subject somatic cell with PDGF-AB and Azacitidine for a time and under conditions sufficient to induce said transition.

Without limiting the invention in any way, platelet-derived growth factor (PDGF) is one of the numerous growth factors that regulate cell growth, migration and division. In particular, it plays a significant role in blood vessel formation (angiogenesis) and the growth of blood vessels from already-existing blood vessel tissue. PDGF is a dimeric glycoprotein composed of two A (-AA) or two B (-BB) subunit chains or a combination of the two (-AB). In both mouse and human, the PDGF signalling network consists of four ligands, PDGFA-D, and two receptors, PDGFRalpha and PDGFRbeta. All PDGFs function as secreted, disulphide-linked homodimers, but only PDGFA and B can form functional heterodimers. There are five different isoforms of PDGF that activate cellular response through two different receptors. Known ligands include A (PdgfA), B (PdgfB), C (PdgfC), and D (PdgfD), and AB heterodimer. Reference to "PDGF-AB" should therefore be understood as a reference to all forms of PDGF-AB and to functional mutant or polymorphic forms of this molecule. Reference to "PDGF-AB" should also be understood to include all precursor, proprotein or intermediate forms thereof.

PDGF-A and PDGF-B are produced from different genes and form a heterodimer intracellularly. Typically, in accordance with embodiments of the present invention the PDGF-AB heterodimer employed comprises the amino sequences of human PDGF-A (Accession No. P04085; SEQ ID NO:1) and human PDGF-B (Accession No. P01127; SEQ ID NO:2).

"Derivatives" of PDGF-AB include functional fragments, parts, portions, variants, mutants or orthologues from either natural or non-natural sources. Non-natural sources include, for example, recombinant or synthetic sources. By "recombinant sources" is meant that the cellular source from which the subject molecule is harvested has been genetically altered. This may occur, for example, in order to increase or otherwise enhance the rate and volume of production by that particular cellular source. Parts or fragments include, for example, active regions of the molecule. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above. Derivatives also include fragments having particular epitopes or parts of the entire protein fused to peptides, polypeptides or other proteinaceous or non-proteinaceous molecules.

A "variant" or "mutant" of PDGF-AB should be understood to mean molecules which exhibit at least some of the functional activity of the form of PDGF-AB of which it is a variant or mutant. A variation or mutation may take any form and may be naturally or non-naturally occurring.

By "orthologue" is meant that the molecule is derived from a species other than that which is being treated in accordance with the method of the present invention. This may occur, for example, where it is determined that a species other than that which is being treated produces a form of PDGF-AB, which exhibits similar and suitable functional characteristics to that of the PDGF-AB which is naturally produced by the subject undergoing treatment.

Reference hereinafter to PDGF-AB is to be understood as being reference to PDGF-AB or functional derivative, fragment or mimetic thereof.

Azacitidine, also known as 5-Azacitidine, is a chemical analogue of cytosine, a nucleoside present in DNA and RNA. Without limiting the invention in any way, Azacitidine is thought to inhibit DNA methyltransferase causing hypomethylation of DNA. As azacitidine is a ribonucleoside, it incorporates into RNA to a larger extent than into DNA. The incorporation into RNA leads to the dissembly of polyribosomes, defective methylation and acceptor function of transfer RNA, and inhibition of the production of protein. Its incorporation into DNA leads to a covalent binding with DNA methyltransferases.

Reference herein to "Azacitidine" should be understood as a reference to all forms of this molecule and to functional derivatives and analogues thereof. As detailed above, Azacitidine is an analogue of cytosine in which the pyrimidin-2-one moiety has been replaced with a triazin-2-one moiety. The chemical formula and name for Azacitidine is as follows:

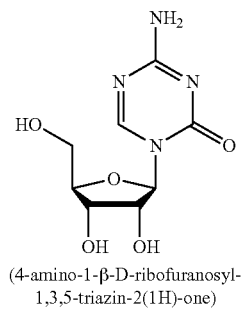

(4-amino-1-β-D-ribofuranosyl-1,3,5-triazin-2(1H)-one)

Reference to Azacitidine should also be understood to encompass reference to any other functional derivative, analogue or molecule which can mimic Azacitidine functional activity. An exemplary analogue is Decitabine:

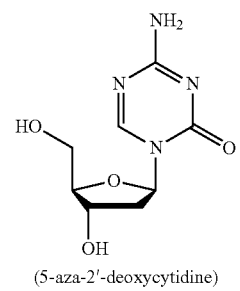

(5-aza-2'-deoxycytidine)

Alternatively, a derivative od Azacitidine may have the formula

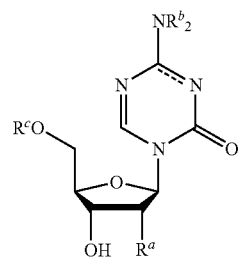

wherein $R^a$ is H or hydroxy;
$R^b$ and $R^c$ are independently H or a $C_{1-6}$ alkyl: and
the dashed line represents an optional bond;

Reference hereinafter to Azacitidine is to be understood as being reference to Azacitidine or functional derivative or analogue thereof.

As detailed hereinbefore, the method of the present invention is predicated on culturing a population of somatic cells with PDGF-AB and Azacitidine to induce de-differentiation to a mesenchymal stem cell phenotype. In one embodiment, said somatic cells are cultured either in vitro or in vivo, in the presence of both PDGF-AB and Azacitidine until such time as a mesenchymal stem cell phenotype is achieved. In another embodiment, one may culture for a period of time in the presence of both PDGF-AB and Azacitidine, followed by a period of culture in the presence of PDGF-AB alone. This latter embodiment may also be performed either in vitro, or in vivo. To the extent that the method is performed in vitro a culture period of about 12-72 hours in the presence of both PDGF-AB and Azacitidine followed by 7-12 days with PDGF-AB alone may be used. The period of culture in the presence of PDGF-AB and Azacitidine may, for example, be about 12 hours, about 24 hours, about 36 hours, about 48 hours, about 60 hours or about 72 hours. In a particular embodiment, the period of culture in the presence of PDGF-AB and Azacitidine may, for example, be about 48 hours. The subsequent period of culture in the presence of PDGF alone may be about 7 days, about 8 days, about 9 days, about 10 days, about 11 days or about 12 days. In a particular embodiment, the period of culture in the presence of PDGF-AB alone is about 10 days. It will be appreciated that establishing appropriate culture conditions, including culturing time is a matter of routine procedure for the person of skill in the art.

Accordingly, in particular embodiments, said somatic cells are cultured with PDGF-AB and Azacitidine together followed by culture with PDGF-AB alone.

To the extent that methods of the present invention are performed in vitro on an isolated population of mature somatic cells, for example fibroblasts, it should be understood that the subject cells may have been freshly isolated from an individual (such as an individual who may be the subject of treatment) or they may have been sourced from a non-fresh source, such as from a culture (for example, where cell numbers were expanded and/or the cells were cultured so as to render them receptive to differentiation signals) or a frozen stock of cells (for example, an established fibroblast cell line), which had been isolated at some earlier time point either from an individual or from another source. It should also be understood that the subject cells may have undergone some other form of treatment or manipulation, such as but not limited to enrichment or purification, modification of cell cycle status or the formation of a cell line. Accordingly, the subject cell may be a primary cell or a secondary cell. A primary cell is one which has been isolated from an individual. A secondary cell is one which, following its isolation, has undergone some form of in vitro manipulation such as the preparation of a cell line, prior to the application of the method of the invention.

It should be understood that embodiments of the present invention also contemplate methods of inducing the differentiation of the mesenchymal stem cells (MSC) which are produced in accordance with the present invention to more mature phenotypes. For example, mesenchymal stem cells can give rise to a wide variety of connective tissues including bone, cartilage, smooth muscle, tendon, ligament, stroma, marrow, dermis and fat. To the extent that it is one or more of these more fully differentiated cell types which is the subject of interest, methods of the invention can be adapted, either in vitro or in vivo, to include a step(s) which introduces the subject mesenchymal stem cells to the specific stimuli required to effect partial or full differentiation along the lineage of interest.

It should also be understood that although this additional directed differentiation event is conveniently performed in vitro, it could also be achieved in vivo. This is discussed in more detail hereinafter. However, a specific in situ environment may also conveniently provide the range of signals required to direct the differentiation of mesenchymal stem cells along a particular lineage.

Reference to "MSC-derived cells" should therefore be understood as a reference to cell types which are more differentiated than a mesenchymal stem cell and which have arisen from the mesenchymal stem cell of the present invention. These cells will correspond to cells of the lineages to which mesenchymal stem cells are known to give rise, such as connective tissue. It should be understood that the subject MSC-derived cell may be a more differentiated precursor cell which is irreversibly committed to differentiating along a particular subgroup of cellular lineages or it may correspond to a partially or terminally differentiated form of a specific cellular lineage, such as a smooth muscle. It should therefore be understood that the cells falling within the scope of this aspect of the present invention may be at any post-mesenchymal stem cell differentiative stage of development. As detailed hereinbefore, this further differentiation may occur constitutively or it may require one or more further signals. These signals may be provided either in vitro, such as in the context of small scale in vitro tissue culture or large scale bioreactor production, or in an in vivo microenvironment, such as if a precursor cell is transplanted into an appropriate tissue microenvironment to enable its further differentiation.

Accordingly, an aspect of the present invention provides a method of facilitating the generation of a mammalian MSC-derived cell, said method comprising:
(i) contacting a somatic cell exhibiting a mature phenotype with PDGF-AB or functional derivative, fragment or mimetic thereof and Azacitidine or functional derivative or analogue thereof for a time and under conditions sufficient to induce the transition of said somatic cell to a mesenchymal stem cell; and optionally
(ii) contacting the mesenchymal stem cell of step (i) with a stimulus to direct the differentiation of said mesenchymal stem cell to a mesenchymal phenotype.

In one embodiment, said somatic cell is a mesenchyme-derived somatic cell, such as a fibroblast, adipocyte, chondrocyte or osteocyte.

According to this embodiment there is therefore provided a method of facilitating the generation of a mammalian MSC-derived cell, said method comprising:
(i) contacting a fibroblast, adipocyte, chondrocyte, osteoblast and/or osteocyte with PDGF-AB or functional alternative, fragment or mimetic thereof and Azacitidine or functional derivative or analogue thereof for a time and under conditions sufficient to induce the transition of said cell to a mesenchymal stem cell; and optionally
(ii) contacting the mesenchymal stem cell of step (i) with a stimulus to direct the differentiation of said mesenchymal stem cell to a mesenchymal phenotype.

Said MSC-derived cell may be a connective tissue cell such as a cell of the bone, cartilage, smooth muscle, tendon, ligament, stroma, marrow, dermis or fat.

In the context of this aspect of the invention, it should be understood that there may be produced individual cells as well as cellular aggregates such as tissues (for example, muscular or dermal tissue), and cell suspensions.

As detailed hereinbefore, the present invention is predicated on the determination that stem cells can be generated from mature somatic cells. To this end, it should be understood that this may be achieved either in the context of directing the transition of all the mature somatic cells of a starting population or in the context of directing the transition of a subpopulation of the starting population of mature somatic cells. This is likely to depend, for example, on the purity and/or heterogeneity of the starting cell population. Still further, the culture system of the invention may result in the production of a heterogeneous population of cells. This may occur, for example, if not all the cells of the starting population transition to a mesenchymal stem cell phenotype or if not all the mesenchymal stem cells are induced to differentiate to a more mature and homogeneous phenotype. This being the case, since not all the cells of the starting population may necessarily differentiate to the mesenchymal stem cell phenotype or MSC-derived phenotype, and the MSC-derived cellular output which is obtained may itself be heterogeneous, the method of the invention may require the application of a screening and selection step to identify and isolate cells exhibiting the desired phenotype. Identification methods would be well known to the person of skill in the art and include, but are not limited to:

(i) Detection of Cell Lineage Specific Structures.

Detection of cell lineage specific structures can be performed, for example, via light microscopy, fluorescence affinity labelling, fluorescence microscopy or electron microscopy, depending on the type of structure to be identified. Light microscopy can be used to detect morphologic characteristics. For example, mononuclear cells which are about 10-30 µm in diameter, with round or rod-shaped morphology characteristic of immature cardiomyocytes can be identified. Electron microscopy can be used to detect structures such as sarcomeres, X-bands, Z-bodies, intercalated discs, gap junctions or desmosomes. Fluorescence affinity labelling and fluorescence microscopy can be used to detect cell lineage specific structures by fluorescently labelling a molecule, commonly an antibody, which specifically binds to the structure in issue, and which is either directly or indirectly conjugated to a fluorophore. Automated quantitation of such structures can be performed using appropriate detection and computation systems.

(ii) Detection of Cell Lineage Specific Proteins.

Detection of cell lineage specific proteins, such as cell surface proteins or intracellular proteins, may be conveniently effected via fluorescence affinity labelling and fluorescence microscopy, for example. Specific proteins can be detected in both whole cells and tissues. Alternatively, techniques such as Western immunoblotting or hybridization micro arrays ("protein chips") may be employed. The proteins which can be detected via this method may be any protein which is characteristic of a specific population of cells. For example, classes of precursor/progenitor cell types can be distinguished via the presence or absence of expression of one or more cell surface molecules. In this regard, this method can be utilised to identify cell types via either a positive or negative selection step based on the expression of any one or more molecules. More mature cells can usually be characterised by virtue of the expression of a range of specific cell surface or intracellular proteins which are well defined in the literature. For example, muscle cells and other mesenchymal-derived cell types are well documented in the context of protein expression profiles through the various differentiative stages of development.

(iii) Detection of Cell Lineage Specific RNA or DNA.

This method is preferably effected using RT-PCR or real-time (qRT-PCR). Alternatively, other methods, which can be used include hybridization microarray ("RNA chip") or Northern blotting or Southern blotting. RT-PCR can be used to detect specific RNAs encoding essentially any protein, such as the proteins detailed in point (ii) above, or proteins which are secreted or otherwise not conveniently detectable via the methodology detailed in point (ii).

(iv) Detection of Cell Lineage Specific Functional Activity.

Although the analysis of a cell population in terms of its functioning is generally regarded as a less convenient method than the screening methods of points (i)-(iii), in some instances this may not be the case.

It should be understood that in the context of characterising the population of cells obtained via application of the method of the present invention, any one or more of the techniques detailed above may be utilised.

In terms of either enriching a mature somatic cell population prior to culturing in accordance with the method of the invention or isolating or enriching an in vitro mesenchymal stem cell population derived therefrom there are, again, various well known techniques which can be performed. As detailed hereinbefore, antibodies and other cell surface binding molecules, such as lectins, are particularly useful for identifying markers associated with particular cell lineages and/or stages of differentiation. The antibodies may be attached to a solid support to allow for separation. However, other cell separation techniques include those based on differences in physical characteristics (density gradient centrifugation and counter-flow centrifugal elutriation) and vital staining properties (mitochondria-binding dye rhodamine 123 and DNA-binding dye Hoechst 33342).

Procedures for separation may include magnetic separation, using antibody or lectin-coated magnetic beads, affinity chromatography, "panning" with antibody attached to a solid matrix or any other convenient technique. Other techniques providing particularly accurate separation include fluorescence activated cell sorting, this technique also being applicable to the separation of cells based on morphological characteristics which are discernible by forward vs side light scatter. Whereas these techniques can be applied in the context of either positive or negative selection, additional negative selection techniques include, but are not limited to, the site-directed administration of a cytolytic, apoptotic or otherwise toxic agent. This may be most conveniently achieved via the coupling of such an agent to a monoclonal antibody in order to facilitate its directed delivery. In another example, opsonisation with an antibody followed by complement administration may achieve the same outcome.

These techniques can be performed as either a single-step or multi-step protocol in order to achieve the desired level of purification or enrichment.

Since the proliferative capacity of the cells and tissues produced in accordance with the present invention may be important to a given use, for example to repair or regeneration of damaged tissue, or to test the effects of a therapeutic treatment regime, it may be desirable to screen for cells which are displaying an adequate level of proliferative capacity. Determining the proliferative capacity of cells can be performed by numerous standard techniques. Preferably, determination of proliferation is effected via $^3[H]$-thymidine or $^{125}I$-iododeoxyuridine uptake assay. Alternatively, colorimetric assays employing metabolic dyes such as XTT or direct cell counting may be employed to ascertain proliferative capacity. Proliferation capacity can also be evaluated via the expression of cell cycle markers such as Ki-67.

As detailed hereinbefore, methods of the present invention can be performed either in vitro or in vivo. In terms of in vitro technology, there is now provided means of routinely and reliably producing mesenchymal stem cells or MSC-derived cells on either a small scale or on a larger scale. In terms of small scale production, which may be effected in tissue culture flasks for example, this may be particularly suitable for producing populations of cells for a given individual and in the context of a specific condition. In terms of large scale production, one means of achieving such production in accordance with the method of the invention is via the use of a bioreactor.

Bioreactors are designed to provide a culture process that can deliver medium and oxygenation at controlled concentrations and rates that mimic nutrient concentrations and rates in vivo. Bioreactors have been available commercially for many years and employ a variety of types of culture technologies. Of the different bioreactors used for mammalian cell culture, most have been designed to allow for the production of high density cultures of a single cell type and as such find use in the present invention. Typical application of these high density systems is to produce as the end-product, a conditioned medium produced by the cells. This is the case, for example, with hybridoma production of monoclonal antibodies and with packaging cell lines for viral vector production. However, these applications differ from applications where the therapeutic end-product is the harvested cells themselves, as in the present invention.

Once operational, bioreactors provide automatically regulated medium flow, oxygen delivery, and temperature and pH controls, and they generally allow for production of large numbers of cells. Bioreactors thus provide economies of labour and minimization of the potential for mid-process contamination, and the most sophisticated bioreactors allow for set-up, growth, selection and harvest procedures that involve minimal manual labour requirements and open processing steps. Such bioreactors optimally are designed for use with a homogeneous cell mixture or aggregated cell populations as contemplated by the present invention. Suitable bioreactors for use in the present invention include but are not limited to those described in U.S. Pat. No. 5,763,194, U.S. Pat. Nos. 5,985,653 and 6,238,908, U.S. Pat. No. 5,512,480, U.S. Pat. Nos. 5,459,069, 5,763,266, 5,888,807 and 5,688,687.

With any large volume cell culture, several fundamental parameters require almost constant control. Cultures must be provided with the medium that allows for, in the present invention, stem cell maintenance, mesenchymal cell proliferation, mesenchymal cell differentiation (perhaps in the context of several separate differentiation cultures and conditions) as well as final cell culture/preservation. Typically, the various media are delivered to the cells by a pumping mechanism in the bioreactor, feeding and exchanging the medium on a regular basis. The exchange process allows for by-products to be removed from the culture. Growing cells or tissue also requires a source of oxygen. Different cell types can have different oxygen requirements. Accordingly, a flexible and adjustable means for providing oxygen to the cells is a desired component.

Depending on the particular culture, even distribution of the cell population and medium supply in the culture chamber can be an important process control. Such control is often achieved by use of a suspension culture design, which can be effective where cell-to-cell interactions are not important. Examples of suspension culture systems include various tank reactor designs and gas-permeable plastic bags. For cells that do not require assembly into a three-dimensional structure or require proximity to a stromal or feeder layer such suspension designs may be used.

Efficient collection of the cells at the completion of the culture process is an important feature of an effective cell culture system. One approach for production of cells as a product is to culture the cells in a defined space, without physical barriers to recovery, such that simple elution of the cell product results in a manageable, concentrated volume of cells amenable to final washing in a commercial, closed system cell washer designed for the purpose. Optionally, the system would allow for addition of a pharmaceutically acceptable carrier, with or without preservative, or a cell storage compound, as well as provide efficient harvesting into appropriate sterile packaging. Optimally the harvest and packaging process may be completed without breaking the sterile barrier of the fluid path of the culture chamber.

In terms of the application of the present invention in vivo, means for administering the subject PDGF-AB and Azacitidine would be well known to those of skill in the art. One should also appreciate that although embodiments of the invention can be pursued based on inducing the transition of in situ somatic cells to a mesenchymal stem cell phenotype, this being discussed in more detail hereinafter, one may also elect to administer an exogenous population of somatic cells and thereafter induce their transition to a mesenchymal stem cell phenotype. This may be particularly relevant for patients who are deficient in terms of their in situ somatic cell populations, for example those with severe osteoporosis or other conditions which result in reduced bone mass.

Reference to "inducing" the transition of somatic cells to a mesenchymal stem cell phenotype should be understood as a reference to this transition being effected.

In terms of directing the transition/de-differentiation of a somatic cell to a mesenchymal stem cell or the differentiation of that mesenchymal stem cell to a mature phenotype, reference to "contacting" the somatic cell or mesenchymal stem cell with PDGF-AB, Azacitidine or other stimulus should be understood to be achievable either by actively administering the stimulus to the mammal, or in relation to the differentiation of mesenchymal stem cells in particular, by effecting the release of the mesenchymal stem cell into a microenvironment capable of endogenously providing the necessary differentiation signal. This latter mechanism may be achieved, for example, by effecting the release of mesenchymal stem cells either within the appropriate localised microenvironment or in a manner which facilitates the transfer of the mesenchymal stem cells to the appropriate microenvironment, such as via the circulatory system.

In accordance with these in vivo aspects of the present invention, in one preferred embodiment the multilineage potential cell generated in accordance with the method of the invention is a mesenchymal stem cell and the cell type to which it is ultimately induced to differentiate is a connective tissue cell such as a cell of the bone, cartilage, smooth muscle, tendon, ligament, stroma; marrow, dermis or fat.

The development of the present invention has facilitated the development of means for therapeutically or prophylactically treating subjects. In particular, and in the context of particular embodiments of the present invention, means for treating patients exhibiting inadequate, insufficient or aberrant mesenchymal cellular functioning is provided based on administering to these subjects one or more of:

(i) mesenchymal stem cells or partially or fully differentiated MSC-derived cells which have been generated according to the method of the present invention;
(ii) PDGF-AB, Azacitidine or other stimulus for effecting the in vivo generation of the cells of (i) in accordance with the methods hereinbefore defined.

The method can be applied to a wide range of conditions including, but not limited to bone disorders, damaged or morphologically abnormal cartilage, hernia repair, pelvic floor prolapse surgery using supportive mesh and biological scaffolds, cell therapy for other musculoskeletal disorders, replacement of defective supportive tissues in the context of aging, surgery or trauma, tissue repair or regeneration such as bone or cartilage repair, bone or cartilage regeneration, tendon repair, cardiac tissue repair, reprogramming cancer cells to sensitise them to adjuvant.

Reference to a condition characterised by "aberrant mesenchymal cellular functioning" should be understood as a reference to any condition which is due, at least in part, to a defect or unwanted or undesirable outcome in terms of the functioning or development of cells of the mesenchymal lineages. This may correspond to either a homogeneous or heterogeneous population of cells. Reference to "mesenchymal stem cells" or "MSC-derived cells" should be understood to have the same meaning as defined hereinbefore. The subject defect should be understood as a reference to any structural or functional feature of the cell which is either not normal or otherwise undesirable, including the production of insufficient numbers of these cells.

Accordingly, another aspect of the present invention is directed to a method of therapeutically and/or prophylactically treating a condition in a mammal, said method comprising administering to said mammal:
(i) an effective number of mesenchymal stem cells or partially or fully differentiated MSC-derived cells which have been generated according to the method of the present invention; or
(ii) an effective amount of PDGF-AB, Azacitidine or other stimulus suitable for effecting the in vivo generation of the cells of (i) in accordance with the methods hereinbefore defined.

Reference to "administering" to an individual an effective number of the cells of the invention should be understood as a reference to introducing into the mammal an ex vivo population of cells which have been generated according to the method of the invention. Reference to "administering", a PDGF-AB, Azacitidine or other stimulus to induce stem cell directed differentiation should be understood as a reference to introducing into the mammal an effective amount of one or more stimuli which will act on a somatic cell in vivo, and preferably located in situ, to generate said mesenchymal stem cell or MSC-derived cell. With respect to this latter embodiment, the cell may be one which has always been present in the individual (that is, it has never been removed from the individual) or it may be one which was previously located ex vivo and has been introduced into the individual whereby its in vivo differentiation will subsequently be effected. This may occur where a somatic cell line is created using nuclear material derived from the patient in issue. In this regard, it may be desirable to manipulate, culture, mark or otherwise treat the cell ex vivo in order to prepare it for in vivo differentiation but to conduct the actual steps of mesenchymal stem cell transition and/or subsequent differentiation in the in vivo, and even more preferably in situ, environment.

Said method may be performed by in vivo administration of PDGF-AB and Azacitidine (for example in solution or mixed into a polymer for sustained release) to a localised site in need of tissue repair or regeneration. For example, PDGF-AB and Azacitidine may be delivered via implantable biodegradable or non-biodegradable gels, such as a hydrogel capable of releasing the PDGF-AB and Azacitidine over the required period of time (in particular embodiments being about 48 hours for Azacitidine and 12 days for PDGF-AB. In exemplary embodiments, the PDGF-AB and Azacitidine may be mixed with a poly(vinyl) alcohol (PVA) monomer and subsequently polymerised into a gel. If required, the modify the release rate of the PDGF-AB and/or the Azacitidine the molecules may be covalently bound in the hydrogel, or combined with other compounds to interact with one or more of the PDGF-AB and Azacitidine (such as heparin to interact with PDGF-AB) and retard release. An exemplary suitable non-biodregadable polymer is ethylene vinyl acetate copolymer (EVAc).

In another embodiment, one may harvest autologous cells, mix them with PDGF-AB and Azacitidine and thereafter implant these cells at the site in need of tissue repair or regeneration. By way of example, in situations in which bone repair or regeneration is required, bone may be harvested, either from the individual in need of treatment or from a different individual, mixed with PDGF-AB and Azacitidine, and grafted into the required site (e.g of injury), with or without ex vivo culture. Further, embodiments of the invention contemplate coating implants, such as orthopaedic implants (e.g. hip and knee implants) with PDGF-AB and Azacitidine, prior to introduction into a subject, with or without prior ex vivo culture, to induce bone regeneration. This will, in turn, assist in adherence of the implant to bone, thereby preventing premature implant rejection or failure.

In accordance with treatment methods which involve the administration of an exogenous population of mesenchymal stem cells or MSC-derived cells, the subject cells may be autologous cells which are identified, isolated and/or differentiated to the requisite phenotype ex vivo and transplanted back into the individual from which they were originally harvested. However, it should be understood that the present invention also extends to the use of cells derived from any other suitable source where the subject cells exhibit the same major histocompatibility profile as the individual who is the subject of treatment. Accordingly, such cells are effectively autologous in that they would not result in the histocompatibility problems which are normally associated with the transplanting of cells exhibiting a foreign MHC profile. Such cells should be understood as falling within the definition of "autologous". For example, under certain circumstances it may be desirable, necessary or of practical significance that the subject cells are isolated from a genetically identical twin, or from an embryo generated using gametes derived from the subject individual or cloned from the subject individual. The cells may also have been engineered to exhibit the desired major histocompatibility profile. The use of such cells overcomes the difficulties which are inherently encountered in the context of tissue and organ transplants. However, where it is not possible or feasible to isolate or generate autologous cells, it may be necessary to utilise allogeneic stem cells. "Allogeneic" cells are those which are isolated from the same species as the subject being treated but which exhibit a different MHC profile. Although the use of such cells in the context of therapeutics would likely necessitate the use of immunosuppression treatment, this problem can nevertheless be minimised by use of cells which exhibit an MHC profile exhibiting similarity to that of the subject being treated, such as a cellular population which has been isolated/generated from a relative such as a sibling, parent or child. The present invention should also be understood to extend to xenogeneic transplantation. That is, the cells which are generated in accordance with the method of the invention and introduced into a patient, are isolated from a species other than the species of the subject being treated. It should be understood that these principles also apply to the situation where a population of somatic cells is administered to a patient for the purpose of effecting transition and differentiation in vivo.

Without limiting the present invention to any one theory or mode of action, even partial restoration of the functioning which is not being provided by the aberrant cellular population will act to ameliorate the symptoms of many conditions. Accordingly, reference to an "effective number" means that number of cells necessary to at least partly attain the desired effect, or to delay the onset of, inhibit the progression of, or halt altogether the onset or progression of the particular condition being treated. Such amounts will depend, of course, on the particular conditions being treated, the severity of the condition and individual patient parameters including age, physical conditions, size, weight, physiological status, concurrent treatment, medical history and parameters related to the disorder in issue. One skilled in the art would be able to determine the number of cells and tissues of the present invention that would constitute an effective dose, and the optimal mode of administration thereof without undue experimentation, this latter issue being further discussed hereinafter. These factors are well known to those of ordinary skill in the art and can be addressed with no more than routine experimentation. It is preferred generally that a maximal cell number be used, that is, the highest safe number according to sound medical judgement. It will be understood by those of ordinary skill in the art, however, that a lower cell number may be administered for medical reasons, psychological reasons or for any other reasons.

As hereinbefore discussed, it should also be understood that although methods of the present invention encompass within their scope the introduction of transitioned or fully or partially differentiated cells to an individual suffering a condition as herein defined, it is not necessarily the case that every cell of the population introduced to the individual will have acquired the mesenchymal stem cell or MSC-derived phenotype of interest. For example, where a fibroblast population has undergone transition to mesenchymal stem cells and is administered in total, there may exist a proportion of cells which have not undergone transition to a cell exhibiting the requisite phenotype. The same issue can occur in the context of administering a population of MSC-derived cells, such as specific mesenchymal populations. The present invention is therefore achieved provided the relevant portion of the cells thereby introduced constitute the "effective number" as defined above. However, in a particularly preferred embodiment the population of cells which have undergone differentiation will be subjected to the identification of successfully differentiated cells, their isolation and introduction to the subject individual. This provides a means for selecting either a heterogeneous population of MSC-derived cells, such as may occur where mesenchymal-derived connective tissue is induced to develop, or to select out a specific subpopulation of cells for administration. The type of method which is selected for application will depend on the nature of the condition being treated. However, it is expected that in general it will be desirable to administer a pure population of cells in order to avoid potential side effects such as teratoma formation. Alternatively, in some instances it may be feasible to subject a population of mesenchymal stem cells to differentiation and provided that this population, as a whole, is shown to exhibit the requisite functional activity, this population as a whole may be introduced into the subject individual without the prior removal of irrelevant cell types. Accordingly, reference to "an effective number", in this case, should be understood as a reference to the total number of cells required to be introduced such that the number of differentiated cells is sufficient to produce the level of activity which achieves the object of the invention, being the treatment of the subject condition.

As detailed hereinbefore, mesenchymal stem cell transition and, optionally, directed differentiation of the subject cells, can be performed in vivo or in vitro. In the latter situation, the subject cell will then require introduction into the subject individual. Where the cells are differentiated in vitro, the subject cells are preferably ones which were isolated from the individual to be treated (i.e. autologous cells). However, the present invention nevertheless extends to the use of cells sourced elsewhere, such as syngeneic cells from an identical twin or cells from an embryo which exhibit the same major histocompatibility profile as that of the individual in question. To the extent that the cells are differentiated in vitro, the cells may be subsequently introduced into an individual by any suitable method. For example, cell suspensions may be introduced by direct injection or inside a blood clot whereby the cells are immobilised in the clot thereby facilitating transplantation. The cells may also be encapsulated prior to transplantation. Encapsulation is a technique which is useful for preventing the dissemination of cells which may continue to proliferate (i.e. exhibit characteristics of immortality) or for minimising tissue incompatibility rejection issues. However, the usefulness of encapsulation will depend on the function which the transplanted cells are required to provide. For example, if the transplanted cells are required primarily for the purpose of secreting a soluble factor, a population of encapsulated cells will likely achieve this objective. However, if the transplanted cells are required for their contractile properties, for example, the cells will likely be required to integrate with the existing tissue scaffold of the muscle. Encapsulated cells would not be able to do this efficiently.

The cells which are administered to the patient can be administered as single or multiple doses by any suitable route. Preferably, and where possible, a single administration is utilised. Administration via injection can be directed to various regions of a tissue or organ, depending on the type of repair required.

It would be appreciated that in accordance with these aspects of the present invention, the cells which are administered to the patient may take any suitable form, such as being in a cell suspension or taking the form of a tissue graft (e.g. connective tissue). In terms of generating a single cell suspension, the differentiation protocol may be designed such that it favours the maintenance of a cell suspension. Alternatively, if cell aggregates or tissues form, these may be dispersed into a cell suspension. In terms of utilising a cell suspension, it may also be desirable to select out specific subpopulations of cells for administration to a patient. To the extent that it is desired that a tissue is transplanted into a patient, this will usually require surgical implantation (as opposed to administration via a needle or catheter). Alternatively, a portion, only, of this tissue could be transplanted. In another example, engineered tissues can be generated via standard tissue engineering techniques, for example by seeding a tissue engineering scaffold having the designed form with the cells and tissues of the present invention and culturing the seeded scaffold under conditions enabling colonization of the scaffold by the seeded cells and tissues, thereby enabling the generation of the formed tissue. The formed tissue is then administered to the recipient, for example using standard surgical implantation techniques. Suitable scaffolds may be generated, for example, using biocompatible, biodegradable polymer fibers or foams, comprising extracellular matrix components, such as laminins, collagen, fibronectin, etc. Detailed guidelines for generating or obtaining suitable scaffolds, culturing such scaffolds and therapeutically implanting such scaffolds are available in the literature (for example, refer to Kim S. S. and Vacanti J. P., 1999. *Semin Pediatr Surg.* 8:119, U.S. Pat. No. 6,387,369 to Osiris, Therapeutics, Inc.; U.S. Pat. App. No. US20020094573A1 to Bell E.).

In accordance with methods of the present invention, other proteinaceous or non-proteinaceous molecules may be co-administered either with the introduction of the subject cells or prior or subsequently thereto. By "co-administered" is meant simultaneous administration in the same formulation or in different formulations via the same or different routes or sequential administration via the same or different routes. By "sequential" administration is meant a time difference of from seconds, minutes, hours or days between the introduction of these cells and the administration of the proteinaceous or non-proteinaceous molecules or the onset of the functional activity of these cells and the administration of the proteinaceous or non-proteinaceous molecule. Examples of circumstances in which such co-administration may be required include, but are not limited to:

(i) When administering non-syngeneic cells or tissues to a subject, there usually occurs immune rejection of such cells or tissues by the subject. In this situation it would be necessary to also treat the patient with an immunosuppressive regimen, preferably commencing prior to such administration, so as to minimise such rejection. Immunosuppressive protocols for inhibiting allogeneic graft rejection, for example via administration of cyclosporin A, immunosuppressive antibodies, and the like are widespread and standard practice.

(ii) Depending on the nature of the condition being treated, it may be necessary to maintain the patient on a course of medication to alleviate the symptoms of the condition until such time as the transplanted cells become integrated and fully functional. Alternatively, at the time that the condition is treated, it may be necessary to commence the long term use of medication to prevent re-occurrence of the damage. For example, where the subject damage was caused by an autoimmune condition (such as occurs in the context of rheumatoid arthritis), the ongoing use of immunosuppressive drugs may be required even when syngeneic stem cells have been used to replace or repair cartilage.

It should also be understood that methods of the present invention can either be performed in isolation to treat the condition in issue or can be performed together with one or more additional techniques designed to facilitate or augment the subject treatment. These additional techniques may take the form of the co-administration of other proteinaceous or non-proteinaceous molecules, as detailed hereinbefore.

Another aspect of the present invention is directed to the use of a population of mesenchymal stem cells or MSC-derived cells, which cells have been generated in accordance with methods of the present invention, in the manufacture of a medicament for the treatment of a condition in a mammal.

Yet another aspect of the present invention is directed to an isolated population of mesenchymal stem cells or MSC-derived cells which have been generated in accordance with methods of the present invention.

In a related aspect of the present invention, the subject undergoing treatment or prophylaxis may be any human or animal in need of therapeutic or prophylactic treatment. In this regard, reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of the onset of a particular condition. "Treatment" may also reduce the severity of an existing condition.

The development of a method for generating mesenchymal stem cells and MSC-derived cells in vitro has now facilitated the development of in vitro based screening systems for testing the effectiveness and toxicity of existing or potential treatment or culture regimes.

Thus, according to yet another aspect of the present invention, there is provided a method of assessing the effect of a treatment or culture regime on the phenotypic or functional state of a mesenchymal stem cells or MSC-derived cell said method comprising subjecting said mesenchymal stem cell or MSC-derived cell, which cell has been generated in accordance with a method hereinbefore defined, to said treatment regime and screening for an altered functional or phenotypic state.

By "altered" is meant that one or more of the functional or phenotypic parameters which are the subject of analysis are changed relative to untreated cells. This may be a desirable outcome where the treatment regime in issue is designed to improve cellular functioning. However, where the treatment regime is associated with a detrimental outcome, this may be indicative of toxicity and therefore the unsuitability for use of the treatment regime. It is now well known that the differences which are observed in terms of the responsiveness of an individual to a particular drug are often linked to the unique genetic makeup of that individual. Accordingly, the method of the present invention provides a valuable means of testing either an existing or a new treatment regime on cells which are generated utilising nuclear material derived from the individual in issue. This provides a unique means for evaluating the likely effectiveness of a drug on an individual's cellular system prior to administering the drug in vivo. Where a patient is extremely unwell, the physiological stress which can be caused by a treatment regime which causes an unwanted outcome can be avoided or at least minimised.

Accordingly, this aspect of the present invention provides a means of optimising a treatment which is designed to normalise cellular functioning. However the method can also be used to assess the toxicity of a treatment, in particular a treatment with a compound. Thus, failure to generate a characteristic associated with a haematopoietic or mesenchymal phenotype, for example, in the cells and tissues of the present invention in response to treatment with a compound can be used to assess the toxicity of such a compound.

Hence a method of the present invention can be used to screen and/or test drugs, other treatment regimes or culture conditions. In the context of assessing phenotypic changes, this aspect of the present invention can be utilized to monitor for changes to the gene expression profiles of the subject cells and tissues. Thus, the method according to this aspect of the present invention can be used to determine, for example, gene expression pattern changes in response to a treatment.

Typically, the treatment to which the cells or tissues of the present invention are subjected is an exposure to a compound. Typically, the compound is a drug or a physiological ion. Alternatively the compound can be a growth factor or differentiation factor. To this end, it is highly desirable to have available a method which is capable of predicting such side effects on cellular populations prior to administering the drug.

The present invention is further described by reference to the following non-limiting examples.

EXAMPLES

Methods

Mice

Mouse strains were C57BL/6J, Pdgfra-nGFP (Pdgfra$^{tm11(EGFR)Sor}$)(Hamilton et al., 2003), DMP1-Cre R26eYFP (Tg(Dmp1-cre)1JqfeGtROSA)26Sor) (Stern et al., 2012), Rag1-/- Rag1$^{tm1Mom}$) (Mombaerts et al., 1992) and GreenTg (C57BL/6Tg(UBC-GFP)30Scha/J) (Schaefer et al., 2001). Mice were housed in the Biological Resource Centre at the Lowy Cancer Research Centre, University of New South Wales. All experiments involving mice were approved by the University of New South Wales animal ethics committee.

BM-CFU-F Isolation and Ex Vivo Expansion

BM-CFU-Fs were isolated from wild-type C57BL/6, Pdgfrα-nGFP or DMP1 eYFP mice. The mice were sacrificed at 8-16 weeks of age. Tibias and femurs were removed, cleaned of excess soft tissues and transferred to ice cold PBS (Invitrogen, Carlsbad, Calif.). Bone marrow was flushed out with 2% fetal calf serum (FCS) in PBS and bones were thoroughly crushed using a mortar and pestle. Bone fragments were transferred into collagenase Type II (263 U/ml; Worthington Biosciences, N.J.) and placed on a shaker at 37° C. for 20 min. The supernatant was passed through a 40 μm filter into a fresh tube and inactivated with 100% FCS. Cells were washed twice in 2% FCS in PBS and plated in MEM (Invitrogen, Carlsbad, Calif.) with 20% FCS, and penicillin/streptomycin/glutamine (P/S/G, Invitrogen) and cultured in the incubator at 37° C., 5% $CO_2$ for 72 h. At the end of 72 h cells were washed in PBS to remove non-adherent cells and cultures were continued in fresh medium. Cells were passaged on reaching 80% confluence. After passaging cells, they were placed back in tissue culture flasks (T75) with αMEM+20% FCS+P/S/G for bulk passaging. Cells were routinely cryopreserved in 10% DMSO and 90% culture medium.

Primary Osteocyte Isolation and Culture

Osteocytes were isolated from long bones of either wild-type C57BL/6 or Pdgfra-nGFP mice. The mice were sacrificed at 8-16 weeks of age. Tibias and femurs were removed, cleaned of soft tissues and transferred to ice cold PBS. Bone marrow was flushed out with 2% FCS in PBS and bones were crushed and cut into ~200 μm-400 μm pieces using a mortar and pestle and scissors. Bone fragments were transferred into 5 ml of collagenase (Type II, 2 mg/ml) in PBS and placed on a water bath shaker at 37° C. for 30 min twice. Supernatant was collected and collagenase was inactivated with 10 ml of 2% FCS and 5 mM EDTA in PBS. Cells were collected through 40 μm cell strainer. Cells were stained for Sca1, CD51, CD31, Lin/CD45 and Pdgfrα. These cells were FACS sorted for Sca1$^-$/CD31$^-$/Pdgfra-nGFP$^-$/Pdgfra-Protein$^-$/CD51$^+$ osteocytes. FACS sorted osteocytes and bone fragments were cultured independently in complete culture medium (DMEM+P/S/G+100 ug/ml of ascorbate+10% FCS). Cells were cultured at 37° C. and 5% $CO_2$ in the incubator for 8-10 days. Osteocytes (Sca1$^-$/CD31$^-$/Pdgfra$^-$/CD51$^+$) derived from culturing bone fragments were also FACS sorted before culturing in the reprogramming medium.

Primary Osteocyte Isolation and Culture

Primary osteocytes were isolated from 8-16 weeks old DMP1eYFP mice derived long bones (femurs and tibia) using a previously described method (Stern et al., 2012). Cell suspensions resulting from the primary isolation procedure and resulting bone fragments were cultured on type-I rat tail collagen-coated six-well plates at a density of 25,000 cells per cm$^2$ and 20-30 bone fragments per well respectively in osteocyte culture medium (αMEM+5% FCS+P/S/G). Cells were maintained at 37° C. and 5% $CO_2$ in the incubator for 7 days. Cells were cultured from suspension and the outgrowths of cells from bone fragments were FACS sorted for Sca1$^-$/CD31$^-$/Pdgfra$^-$/Dmp1eYFP$^+$ and cultured in osteocyte culture media for 3 days before replaced with the reprogramming medium.

Cellular Reprogramming and Inhibitor Studies

In vitro differentiated bone, cartilage, fat and long-bone derived osteocytes were first cultured in MSC medium (αMEM+20% FCS+P/S/G) with or without 10 μM 5'Azacitidine (Tocris Biosciences) and with or without cytokine (50 or 100 ng/ml Pdgf-AA or Pdgf-BB or Pdgf-AB, 10 ng/ml bFgf, 20 ng/ml HGF, 10 ng/ml Igf-1 and 10 ng/ml Vegf for 2 days and then cultured in MSC media with or without cytokine for 10 days. In order to investigate the reprogramming cell signalling pathways, inhibitors were added to the reprogramming cocktail from day 1 and kept for 12 days. Media was refreshed every 3-4 days. At the end of day 12 cells were harvested for downstream analysis.

In Vivo Imaging

Changes in cellular morphology and GFP expression in individual osteocytes derived from Pdgfrα-GFP mice and change in cellular morphology and acquisition of proliferative capacity in Dmp1-eYFP$^+$ osteocytes was established by live imaging using an IncuCyte microscope (Essen Bioscience) with 10× phase objective and a Nikon Ti-E microscope with a 20× phase objective (0.45 NA). Images were captured every 60 and 30 mins respectively for 8 days. 12 bit images were acquired with a 1280×1024 pixel array.

CFU-F Long-Term Growth and Serial Clonogenicity

CFU-Fs, oCFU-Fs, cCFU-Fs and aCFU-Fs were expanded in bulk culture after plating 10,000 cells per T75 flask. Resulting cells were split every 8 days. CFU-F and oCFU-F colonies were isolated individually using cloning cylinders ('O' rings) (Sigma-Aldrich) and CFU-F clones (micro, small and large) and Osteocyte oCFU-F clones (micro, small and large) were pooled individually as micro (MC), small (SC) and large (LC) colonies and cultured first in T25 flask for 12 days and then from passage 2 onwards in T75 flask for 12 days. Cumulative cells numbers were calculated and plotted (log 10 scale). Micro, small and large colony's 2ry, 3ry and 4ry colony formation was evaluated by plating single cell from individual colonies into 96 well plates. In order to investigate differences in proliferative capacity of reprogrammed cells compared with primary CFU-Fs, cells were plated on RTCA resistor plate 96 (Roche Diagnostics) (200 cells/well) and recorded using XCELLigence (ACEA Biosciences) every 15 mins for 8 days.

In Vitro Lineage Differentiation

Osteogenic differentiation: Osteogenic differentiation was promoted by culturing cells in either 6 well plate or in 4 chamber slide containing Dulbecco's Minimum Essential Medium-low glucose (DMEM-LG) (Invitrogen, Calif.), 10% FCS, 100 µg/ml penicillin and 250 ng/ml streptomysin, 200 mM L-Glutamine and 0.1 µM dexamethasone, 10 mM-glycerophosphate, 200 µM L-ascorbic acid 2-phosphate for 21 days. The cells were stained with alizarin Red and anti-Runx2 antibody.

Chondrogenic differentiation: $2.5\times10^5$ to $1\times10^5$ cells were plated either in 6 well plate or 4 well chamber slide contained serum free Dulbecco's Minimum Essential Medium high glucose (DMEM-HG), 100 µg/ml penicillin and 250 ng/ml streptomycin, 200 mM L-Glutamine, 50 µg/ml insulin-transferrinselenious (ITS) acid mix (BD Biosciences), 2 mM L-ascorbic acid 2-phosphate, 1 mM sodium pyruvate, 0.1 µM dexamethasone, and 10 ng/ml transforming growth factor β3 (TGF-β3). Medium was changed every 4 days for 28 days. Differentiated cells were stained for sulfated proteoglycans with 1% alcian blue and anti-Sox9 antibody.

Adipogenic Differentiation: Cells were cultured in DMEM-HG containing 10% FCS, 100 µg/ml penicillin and 250 ng/ml streptomycin, 200 mM L-Glutamine and 0.5 µM 1methyl=3-isobutyl methylxantine, 1 µM dexamethasone, 10 µg insulin, 200 µM indomethacin. Cells were cultured for 7-10 days. The cells were fixed and stained with Oil Red O or anti-Pparg antibody.

Smooth muscle differentiation: Smooth Muscle differentiation was promoted by culturing the cells in the presence of 50 ng/ml Platelet derived growth factor BB (Pdgf-BB) made up with 5% FCS in DMEM-HG and 100 µg/ml penicillin and 250 ng/ml streptomycin and 200 mM L-Glutamine. The cells were induced for 14 days with media changed every 3-4 days. The cells were stained for smooth muscle myosin heavy chain (MYH1), Myocardin (MYOCD), Serum response factor (SRF) and calponin.

Endothelial differentiation: Endothelial cell differentiation was promoted by culturing the cells in 5%, FCS in Iscove's modified Dulbecco's Medium (Invitrogen, Calif.) containing 10 ng/ml bFGF and 10 ng/ml vascular endothelial growth factor (Vegf), 100 µg/ml penicillin and 250 ng/ml streptomycin and 200 mM L-Glutamine. Cells were stained for CD31, VE-Cadherin (VE-Cad), Caviolin-1 (Cavi), von-willebrand's factor (vWF) and endothelial nitric oxide synthase (eNOS). For low density lipoprotein (LDL) uptake, acetylated apoprotein-LDL (AcLDL-Alexa Fluor 488-Molecular probes) at final concentration of 10 ug/ml was added to endothelial differentiation assays at the end of day 14. Then cells were cultured for a further 24 h. At the end of day 15 cells were fixed and uptake was assessed by fluorescence yield. For matrigel assay, CFU-Fs, oCFU-F and osteocytes were plated on the chamber slides containing matigel and cultured for 7 days. At the end of day 7 tubes were fixed and stained for CD31 and Pdgfrb expression.

Cardiomyocyte differentiation: To promote cardiomyocyte differentiation, cells were first cultured in 2% matrigel coated chamber slides or glass bottom petri dishes in normal CFU-F medium for approximately 4-5 days. Then cells were differentiated towards cardiomyocytes in cardiomyogenic differentiation medium consisting of DMEM-LG: Medium 199 (4:1), 1.0 mg/ml bovine insulin, 0.55 mg/ml human transferrin, 0.5 µg/ml sodium selenite, 50 mg/ml bovine serum albumin, and 0.47 µg/ml linoleic acid, 10-4 M ascorbate phosphate, 10-9 M dexamethasone, 100 µg/ml penicillin and 250 ng/ml streptomycin, 200 mM L-Glutamine and 10% FCS with 1 ng/ml recombinant human neuregulin 1β2 for 14-21 days. Fresh medium was changed every 3 days. The cells were stained for cardiac-sarcomeric actinin, Connexin 43, GATA4, Mef2c and NKX 2-5. Beating cardiomyocytes images were acquired on a Nikon Ti-E microscope with a 20× phase objective (0.45 NA). 1000 frames were acquired continuously with a 52 ms frame rate. 12 bit images were acquired with a 1280×1024 pixel array. For cell contraction frequency, we created customized software that used normalized cross-correlation to track the displacement of a user specified region over consecutive frames. Peak detection was performed on pixel displacement values to identify the occurrence of a contraction, which was subsequently used to calculate the beating frequency.

Neuronal differentiation: When the cells reached 80% confluence, culture media was switched to DMEM-HG media containing 100 µg/ml penicillin, 250 ng/ml streptomycin, 200 mM L-Glutamine. and 1 mM-mercaptoethanol. Media was changed every 3-4 days and cultured for 8-10 days. Neural differentiation was confirmed by expression of Glial fibrillary Acidic Protein (Gfap), Neuron specific beta III Tubulin (Tuj1), Oligodendrocyte marker O4.

Hepatocyte differentiation: At 80% cell confluence, culture media was switched to serum free DMEM-HG containing 100 µg/ml penicillin, 250 ng/ml streptomycin, 200 mM L-Glutamine, 20 ng/mL EGF and 10 ng/mL of bFGF to inhibit cell proliferation for 2 days. After conditioning the cells, differentiation medium was added consisting of DMEM-HG supplemented with 20 ng/mL of HGF and 10 ng/mL of bFGF for 7 days. The cells were then cultured in DMEM-HG supplemented with 20 ng/mL OSM, 1 mol/L dexamethasone, 10 L/mL ITS premix and 100 µg/ml penicillin and 250 ng/ml streptomycin for 14 days. Media was changed every 7 days. Hepatic differentiation was assessed by immunofluorescence staining for albumin (Alb) and hepatocyte nuclear factor 4 alpha (Hnf4a).

Teratoma Formation

Rag1 Mice were anaesthetised and the kidney was exposed through an incision on the dorsal lumbar region. $1\times10^6$ cells in 20 ul of PBS containing 30% matrigel were injected under kidney capsule using a fine needle (26G). Rag1 mice were injected with mouse HM1 embryonic stem (ES) cells (N=2) or CFU-Fs (N=3), osteocytes (N=3) and oCFU-Fs (N=3) from 2-microglobulin-GFP mice either alone or as a mixture of mESCs and CFU-Fs (N=3), osteocytes (N=3) or oCFU-Fs (N=3) (mESCs: cells; 1:3). Mice were sacrificed 4-6 weeks after injection. Tumour tissues were fixed in 4% PFA for 48 hrs. Half of the tissue collected from each mouse was embedded in OCT embedding medium while the other half was processed with paraffin embedding. GFP expression was revealed by using immunohistochemistry with biotin conjugated anti-GFP antibody with secondary HRP staining or by immunofluorescence staining as described below with confocal microscope.

Immuno-histochemistry: Cells were washed with PBS for 10 minutes. The cells were then fixed with 4% paraformaldehyde in PBS (w/v) for 15-20 min and permeabilised with 0.03% Tween-20 in PBS (v/v) for 15 min at room temperature. The cells were washed once with PBS and then blocked with 10% donkey serum (v/v) in PBS for 1 h. The cells were subsequently incubated overnight at 4° C. with the primary antibodies in 2% bovine serum albumin (BSA) (w/v) in PBS, stained accordingly with secondary antibodies in 2% BSA and incubated for 1 h at 4° C. Nuclear staining was done with DAPI. Slides were mounted with Prolong-gold mounting medium. Slides were analysed using either L780 LSM Zeiss confocal microscope or Leica SP5 CW STED confocal microscope. 3D rendering was performed using Imaris software in order to provide improved spacial information in Z-direction. 3D isosurface renderings from confocal z-stacks of CFU-Fs and oCFU-Fs cultured in matrigel for 7 days were created. Oil red O, alizarin red and alcian blue staining for adipocytes, osteocytes and chondrocytes respectively analysed by Nikon light microscope.

Immunoblotting and Densitometry

Cell pellets were lysed in non-denaturing lysis buffer containing Complete Protease inhibitor cocktail (Roche) and PhosStop (Roche), followed by brief sonication using Bioruptor (Diagenode). The supernatant of the whole-cell extracts were loaded onto NuPage 4-12% Bis-Tri Gel (Life Technology) and transferred using iBlot Gel Transfer Kit (Nitrocellulose, Life Technology) according to the manufacturers instructions. Densitometry was performed using GE ImageQuant TL Software Version 7.0.

Gene Expression and Epigenetic Analyses

Primers are listed in Table 1 and provided in the Sequence Listing following the specification.

TABLE 1

Primers

| SEQ ID | Gene | Assay | Sequence (5'-3') |
|---|---|---|---|
| 3 | Oct4 (NM_013633.3) | RT-PCR (Forward) | TCTTTCCACCAG GCCCCCGGCTC |
| 4 | Oct4 | RT-PCR (Reverse) | TGCGGGCGGACA TGGGGAGATCC |
| 5 | Nanog (NM_028016.2) | RT-PCR (Forward) | AGGACAGGTTTC AGAAGCAGA |
| 6 | Nanog | RT-PCR (Reverse) | CCATTGCTAGTC TTCAACCACTG |
| 7 | Sox2 (NM_011443.3) | RT-PCR (Forward) | TAGAGCTAGACT CCGGGCGATGA |
| 8 | Sox2 | RT-PCR (Reverse) | TTGCCTTAAACA AGACCACGAAA |
| 9 | Klf4 (NM_010637.3) | RT-PCR (Forward) | GCGAACTCACAC AGGCGAGAAACC |
| 10 | Klf4 | RT-PCR (Reverse) | TCGCTTCCTCTT CCTCCGACACA |
| 11 | cMyc (NM_001177353.1) | RT-PCR (Forward) | TGACCTAACTCG AGGAGGAGCTGG AATC |
| 12 | cMyc | RT-PCR (Reverse) | AAGTTTGAGGCA GTTAAAATTATG GCTGAAGC |
| 13 | Rex1 (NM_009556.3) | RT-PCR (Forward) | ACGAGTGGCAGT TTCTTCTTGGGA |
| 14 | Rex1 | RT-PCR (Reverse) | TATGACTCACTT CCAGGGGGCACT |
| 15 | βActin (NM_007393.3) | RT-PCR (Forward) | CCTAAGGCCAAC CGTGAAAAG |
| 16 | βActin | RT-PCR (Reverse) | TCTTCATGGTGC TAGGAGCCA |
| 17 | Runx2 (NM_001145920) | NOMe-Seq (Forward) | TTTTGYTTTTA GAGGYTTAATTT TATAGGAG |

TABLE 1-continued

Primers

| SEQ ID | Gene | Assay | Sequence (5'-3') |
|---|---|---|---|
| 18 | Runx2 | NOMe-Seq (Reverse) | TATTCCTRCATA AACTATAATTAA ARCACTCACTA |
| 19 | Runx2 | NOMe-Seq (Reverse nested) | CTAAAAAAATT TRCACCRCACTT ATAATTCTA |
| 20 | Pou5f1 (Oct4) (NM_013633) | Bisulfite seq (Forward) | GAYGTTTTTAAT TTTYGTTTGGAA GATATAG |
| 21 | Pou5f1 | Bisulfite seq (Reverse) | YAACATAAAAAA ATCCCCAATACC TCTA |
| 22 | Nanog (NM_028016) | Bisulfite seq (Forward) | GTTTATGGTGGA TTTTGYAGGTGG GATTAAT |
| 23 | Nanog | Bisulfite seq (Reverse) | TCTTCRAAAACT AAATTCCTTACC ARCCTCTA |
| 24 | Nanog | Bisulfite seq (Reverse nested) | CTTACCARCCTC TATRCAAARCAT CTCAA |
| 25 | Klf4 (NM_010637) | Bisulfite seq (Forward) | YGYGGAGTTTGT TTATTTAGYTAT TATGGT |
| 26 | Klf4 | Bisulfite seq (Reverse) | CRCRAAATACRA AATCCTAAAAAC TATAC |
| 27 | Sox2 (Region 1) (NM_011443) | Bisulfite seq (Forward) | GYGTTTTATTTA TTTTTATGTATT TAAGAGAGAGT |
| 28 | Sox2 (Region 1) | Bisulfite seq (Reverse) | AATAAACAACCA TCCATATAATAA AAACTATCAA |
| 29 | Sox2 (Region 2) | Bisulfite seq (Forward) | AGAAGTTTGGAG TTYGAGGTTTAA GT |
| 30 | Sox2 (Region 2) | Bisulfite seq (Reverse) | TTCAACTCCRTC TCCATCATATTA TACATA |
| 31 | Myc (Region 1) | Bisulfite seq (Forward) | GAATAATYGTAT AGAAAGGGAAAG GATTAG |
| 32 | Myc (Region 1) | Bisulfite seq (Reverse) | CRAAAAACTTCT TTTATACTACRA CTCAA |
| 33 | Myc (Region 2) | Bisulfite seq (Forward) | TTGGAAGAGTYG TGTGTGTAGAGT |
| 34 | Myc (Region 2) | Bisulfite seq (Reverse) | CAACTCRAAAAA CTCTTTTCAAAA AAACTAATC |

Total RNA (>200 nt) was prepared from cells using Qiagen's RNeasy mini kit (Qiagen, Germany) as per manufacturer's instructions. High-quality RNA (average RIN>9) was profiled using Illumina's Mouse WG-6 v2.0 Bead arrays. Raw probe level data from the arrays was extracted using Illumina's GenomeStudio program, normalized using LIMMA and differentially expressed genes were identified using BeadArray packages in R/Bioconductor and GenePattern. Pathway analyses of differentially expressed genes were performed using Gene Set Enrichment Analysis and IPA (Ingenuity® Systems). Array data has been deposited in the Gene Expression Omnibus under accession GSE49798.

Allelic bisulphite sequencing. Allelic bisulphite sequencing was performed as described previously (Hesson and Ward, 2013). Briefly this involved sodium bisulfite modification using the EZ DNA methylation Gold Kit (Zymo Research). Analysed regions were amplified from 40 ng of bisulfite treated DNA. PCR products were cloned by ligation and transformation using the TOPO TA Cloning kit (Invitrogen). Individual molecules were isolated from transformed colonies by colony PCR before sequencing using BigDye Terminator v3.1 (ABI).

Nucleosome occupancy and methylome sequencing (NOMe-Seq). NOMe-Seq was performed as described previously (Hesson et al., 2013). This involved treatment of intact nuclei with 200 U GpC methyltransferase M.CviPI for 15 min at 37° C. followed by termination of the reaction with an equal volume of 20 mM Tris HCl pH 7.9, 600 mM NaCl, 1% (w/v) SDS and 10 mM EDTA. Extracted DNA was bisulfite converted and amplified. M.CviPI enzyme methylates accessible DNA at GpC sites, whereas nucleosome bound DNA is inaccessible and remains refractory to GpC methylation. PCR amplicons were cloned and individual molecules sequenced as described above. Regions of M.CviPI inaccessibility of 150 bp were identified as nucleosome occupied.

Principal Component Analysis

Genome-wide gene expression was acquired from EOGEOD-21404 (fetal liver LSK), E-GEOD-21516 (MEF, ESC, EpiSC), E-TABM-1050 (WT) and E-GEOD-36484 (NSC, ESC) using Illumina bead arrays. When merging data between these arrays 25697 probes (18121 genes) were common to all experiments. The resulting dataset was first quantile normalized and the resulting expression values were scaled to the same mean and standard deviation across samples. PCA was performed on whole array data as described earlier (Diffner et al., 2013) and mean of the first two principle components (PCs) was plotted.

Posterior-Lateral Inter-Transverse Lumber Fusion Model

Long bones (femurs and tibias) were harvested from 2-microglobulin-GFP mice, soft tissues were carefully removed and bone marrow was flushed out with cold 2% FCS in PBS in an aseptic manner. The bones were washed twice with cold PBS and crushed using a mortar and pestle then cut into ~200 μm-400 μm pieces. These bone fragments were transferred to 5 ml of collagenase type II (2 mg/ml) in PBS and placed on a water bath shaker at 37° C. for 30 min. This procedure was done three times. Supernatant was removed and the bone fragments were cultured in a) MSC media only for 12 days, b) MSC media+10 uM Azacitidine for 2 days then in MSC media for 10 days, c) MSC media+100 ng/ml PDGF-AB for 12 days and d) MSC media+10 uM Azacitidine+100 ng/ml PDGF-AB for 2 days, then MSC media+100 ng/ml PDGF-AB for 10 days. At the end of day 12 bone fragments were surgically implanted under anaesthesia into posterior-lateral lumbar spine region (L4-L5) bilaterally on Rag1 mice. At the end of 6 and 12 weeks mice were euthanized and analysed by micro-computed tomography (micro CT). Then the spine from the thoracic to caudal vertebral region was removed as whole, including pelvis. After the animal was sacrificed, the spine-allograft complex was harvested; care was taken not to disturb the spinal fusion region. The specimens were fixed in 4% PFA for 48 hours. After 48 hours of fixation in 4% PFA, spines were decalcified in EDTA and either embedded in OCT or paraffin for immunofluorescence and histology analysis.

Micro CT: The lumbar spine-allograft complex was scanned using micro-CT. Image analysis software (Inveon Research Workplace) was used for visualization and analysis of the spinal fusion.

Histology: After micro CT, samples were decalcified in 14% EDTA solution for routine paraffin histology and cryosection for immunofluorescence imaging. The spine-allograft complexes were sectioned sagittally at 5 μm thickness. Histology was done using Harris hematoxylin and eosin. Histology was qualitatively assessed for integrity, quality, graft viability, degree of bone integration, new bone formation, presence of fibrous tissue interface layer, cellular activity, and Sharpey fibers in a blinded fashion by three independent observers.

Example 1. PDGF-AB in Combination with AZA Reprograms In Vitro Derived Bone, Cartilage and Fat Cells into Multipotent MSC-Like Cells To test whether lineage committed mesodermal cells could be induced to proliferate, bone marrow CFU-Fs (Colony Forming Units-Fibroblast) were harvested from mice, and following in vitro differentiation into bone, cartilage and fat cells, cultured them with different cytokines with and without AZA. Lineage commitment of in vitro differentiated cells prior to treatment was established both by immuno-histochemistry, immunofluorescence and expression signatures (data not shown). Bone cells maintained for 12 days in MSC culture medium supplemented with PDGF-AB and AZA demonstrated colony forming potential that was comparable with that of primary bone marrow CFU-Fs (FIG. 1A). Similar results were obtained with cartilage and fat cells (data not shown). By contrast bone, cartilage and fat cells treated for a similar duration with supplements of basic fibroblast growth factor (bFgf), hepatocyte growth factor (HO, insulin-like growth factor-1 (Igf-1) and vascular growth factor (Vegf), with or without AZA showed either no or limited CFU-F potential (data not shown).

The colony forming potential of plastic adherent cells is not equal. Most cells do not generate colonies upon replating and when they do, the colonies are heterogenous is size. To assess and compare clonal vigour of replated cells, the inventors have developed a system to classify CFU-Fs based on cell number and size (Chong et al., 2011). CFU-Fs from replated primary bone marrow CFU-Fs generated micro (MC-5-24 cells; <2 mm), small (SC→25 cells; 2-4 mm) or large (LC→4 mm) (FIG. 1B). At first passage, bone, cartilage and fat cells exposed to the combination of PDGF-AB and AZA generated almost as many CFU-Fs as primary bone marrow stromal cells although the numbers of large colonies were less (FIG. 1B). Although primary CFU-F colonies were also generated by bone, cartilage and fat cells exposed to bFgf, Hgf, Igf-1 and Vegf (with or without AZA), their numbers were substantially lower than with PDGF-AB and there were few large colonies. Compared with bone, cartilage and fat cells maintained in media (UT), treatment with AZA alone or PDGF-AB alone, also generated CFU-Fs at first passage (FIG. 1B). However, whilst primary bone marrow CFU-F and PDGF-AB and AZA treated bone (oCFU-Fs), cartilage (cCFU-Fs) and fat (aCFU-Fs) cells could be serially passaged over time, colonies generated from cells treated with PDGF-AB alone plateau and failed to replate after a few passages. Colonies generated from cells treated with AZA alone could not be replated at all. CFU-Fs generated by bone, cartilage and fat cells exposed to the other cytokines (with or without AZA) could not be serially replated (data not shown).

When primary bone marrow CFU-Fs were taken through to a second passage, micro colonies failed to generate secondary colonies whereas both small and large colonies did (FIG. 1C). These secondary colonies also demonstrated the heterogeneity that was observed after the first passage. Secondary colonies generated from bone, cartilage and fat cells treated with the combination of PDGF-AB and AZA, were also heterogeneous and varied in type and number from those generated by primary bone marrow CFU-Fs (FIG. 1C). To evaluate these differences, the inventors quantified the proliferative capacity of oCFU-Fs, c-CFU-Fs and a-CFU-Fs at first (P1), second (P2), third (P3) and fourth (P4) passage by XCELLigence. The growth kinetics of each gradually changed and by the fourth passage, they approximated the kinetics of primary bone marrow CFU-Fs (FIG. 1D).

Given the colony forming and growth potential of bone, cartilage and fat cells treated with PDGF-AB and AZA, which suggested that they had been reprogrammed into CFU-Fs, the inventors evaluated these cells for surface expression of MSC markers Sca1, CD90.2, CD105 and CD166. Compared with bone, cartilage and fat cells that were maintained in culture media alone, cells treated with PDGF-AB and AZA for 12 and 2 days respectively, adopted surface immunophenotypes of primary bone marrow CFU-Fs (FIG. 1E). These reprogrammed MSC-like cells that were derived from bone, cartilage and fat cells could themselves be differentiated into bone, cartilage and fat (FIG. 1F; data not shown). Taken together these data show that bone, cartilage and fat cells generated from bone marrow stromal cells can be reprogrammed back to an MSC-like state by transient exposure to PDGF-AB and AZA.

Figure 2:
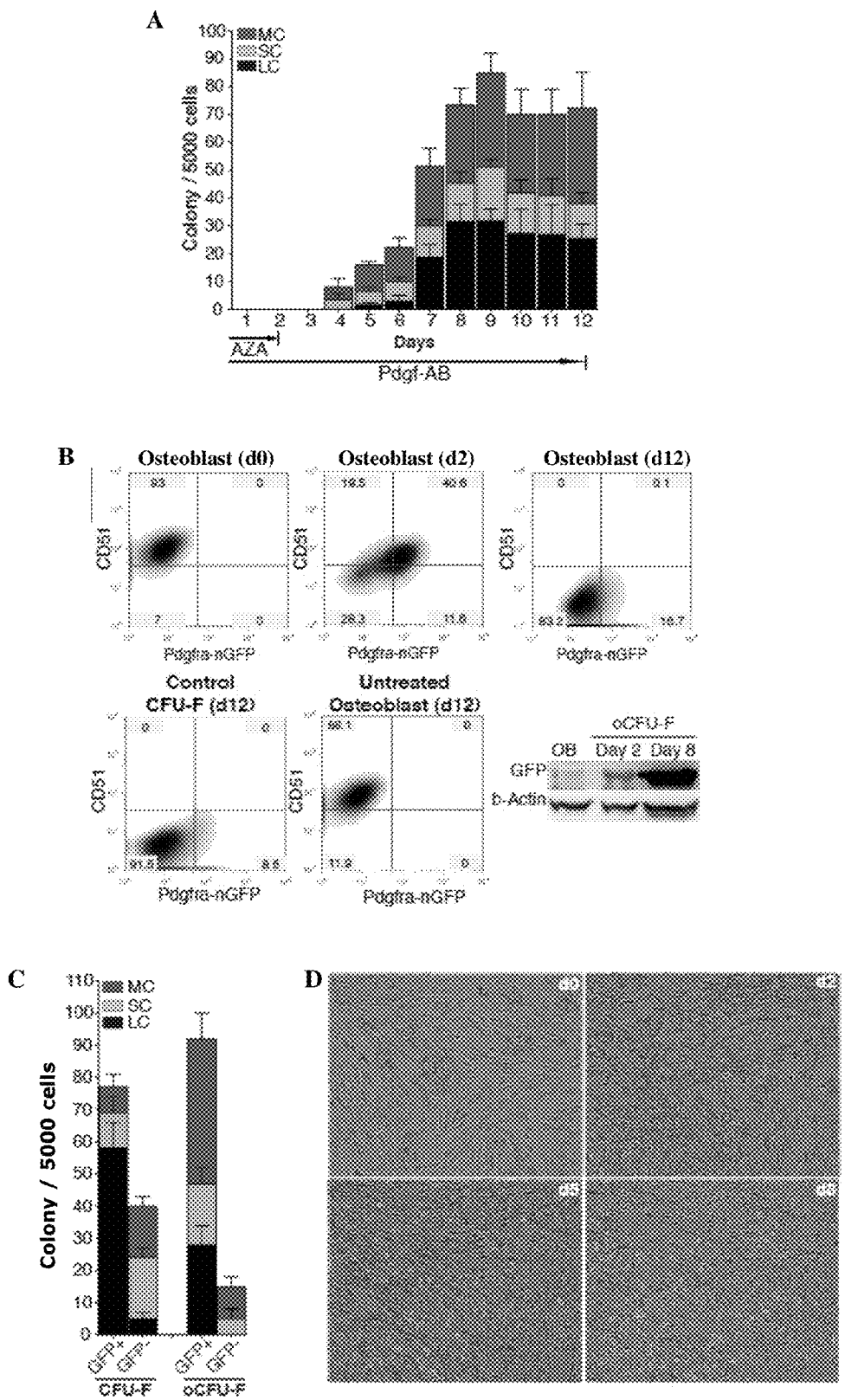
FIG. 2: PDGF-AB in combination with AZA reprograms osteocytes harvested from Pdgfrα-H2B: GFP mice into MSC-like cells. (A) Quantification of CFU-F colonies (based on size) from osteocytes cultured in MSC medium for 12 days supplemented for 1-12 and 1-2 days with PDGF-AB and AZA respectively. (B) Flowcytometry profiles of freshly isolated Pdgfrα-GFP−/CD51+ osteocytes showing progressive loss of CD51 and acquisition of GFP in culture with PDGF-AB and AZA. (C) CFU-F colony number (based on size) derived from sorted bone marrow CFU-Fs and sorted oCFU-Fs. (D) Freshly isolated osteocytes were cultured in MSC medium supplemented with PDGF-AB and AZA and live imaged continuously for eight days with media changes at days 2 and 5. Isolated osteocytes started expressing GFP as early as day 2 with progressive increase in the number of GFP+ cells. (E) Growth curves of micro, small and large colonies from bone marrow CFU-Fs and oCFU-Fs that were harvested at P1 and perpetuated in culture. (F) A clonogenic tree of serial replatings of single micro, small and large colonies from bone marrow CFU-Fs and oCFU-Fs showing type and number of colonies that are generated from each. MC; micro-colony, SC; small-colony, LC; large-colony, CFU-F; colony forming unit-fibroblast, oCFU-F; PDGF-AB/AZA treated osteocytes cultured in MSC medium. Error bars=SEM between independent experiments.
Figure 2:
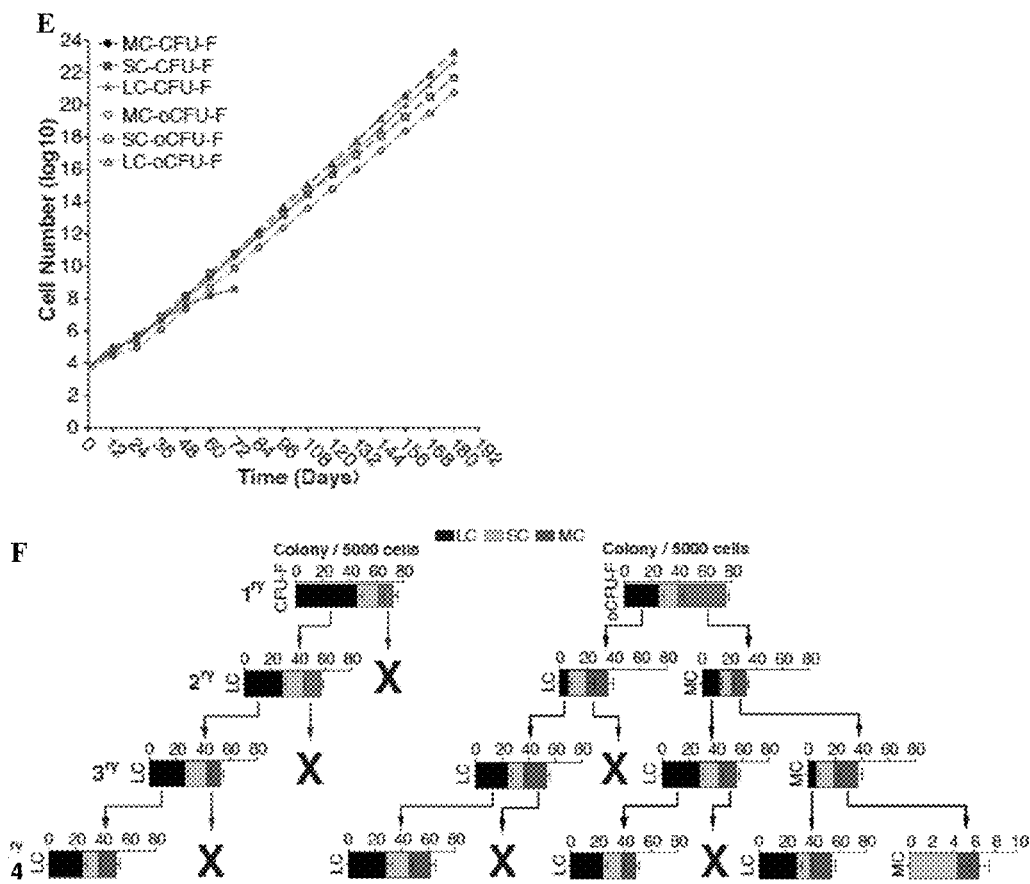

Example 2. PDGF-AB in Combination with AZA Reprograms Osteocytes Harvested from Pdgfrα-H2B:GFP Mice into MSC-Like Cells To evaluate how primary lineage committed cells respond to PDGF-AB/AZA, the inventors harvested Lin$^-$, CD45$^-$/Sca1$^-$/CD31$^-$/Pdgfrα-nGFP$^-$/Pdgfrα$^-$/CD51$^+$ osteocytes from long bones of Pdgfrα-H2B:GFP mice. These cells were plated and left in culture for one week (~70-80% confluence) following which the media was replaced with media supplemented with PDGF-AB and AZA. The emergence of CFU-F capacity in reprogrammed osteocytes was evaluated by replating cells for CFU-F assays from the end of day 1 onwards (FIG. 2A). The CFU-F capacity peaked after eight days of supplementation. Unlike PDGF-AB, osteocytes treated Pdgf-BB (with/without AZA) for 12 days showed very limited CFU-F capacity and could not be passaged (data not shown). Pdgf-AA and AZA treated osteocytes on the other hand did generate CFU-F colonies that could be passaged but their growth potential waned with time (data not shown).

Pdgfrα is expressed by cells with MSC activity. A proportion of freshly harvested (Lin$^-$, CD45$^-$/Sca1$^-$/CD31$^-$/Pdgfrα-nGFP$^-$/Pdgfrα$^-$/CD51$^+$) osteocytes from Pdgfrα-H2B:GFP mice, gained GFP expression and lost CD51 expression when cultured in reprogramming media (FIG. 2B). Pdgfrα-nGFP expression in reprogrammed osteocytes at day 12 was comparable if somewhat higher than in primary bone marrow stromal cells harvested from Pdgfrα-H2B:GFP mice. The colony forming potential in primary bone marrow stromal cells (CFU-Fs) and reprogrammed osteocytes (oCFU-Fs) was predominantly within the Pdgfrα-nGFP positive cell fraction (FIG. 2C). To further correlate the emergence of CFU-F activity in bulk cultures of reprogrammed osteocytes, with Pdgfrα gene expression, the inventors continuously live-imaged osteocytes harvested from Pdgfrα-H2B:GFP mice after the addition of reprogramming media (FIG. 2D). The odd GFP expressing cell was visible as early as day 2 but their number increased progressively from ~day 5 onwards (FIG. 2D). The acquisition of GFP expression by a cell was accompanied by increased motility and cell division.

Figure 3:
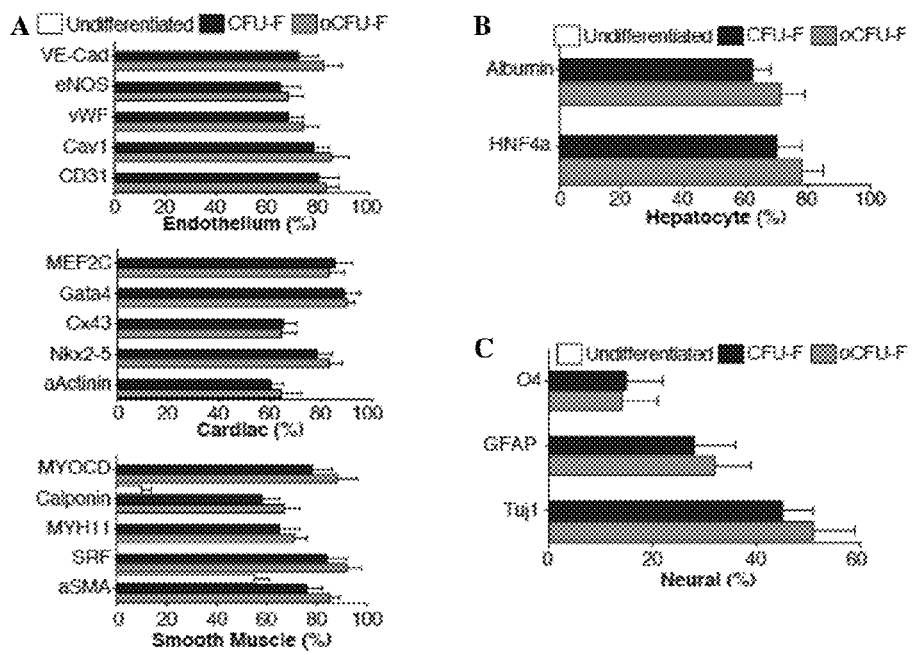
FIG. 3: In vitro and in vivo multipotency of oCFU-Fs derived from Pdgfr☐-H2B:GFP osteocytes. (A) Marker expression for direct in vitro differentiation of oCFU-Fs into mesodermal derivatives; endothelial cells (CD31, VE-Cadherin (VE-Cad), Caveolin (Cavi), von Willebrand factor (vWF), endothelial nitric oxide synthase (eNos) and acetylated low density lipoprotein (ac-LDL) uptake), cardiomyocytes (Nkx2.5, Connexin-43 (CX43), α Smooth muscle actin (aSma), α Cardiac-actinin, Gata4, and show rhythmic spontaneous contractility), smooth muscle (aSma, Calponin, Myosin 11 (Myh11), Myocardin (Myocd) and Serum response factor (Srf)), pericytes/endothelial cells (Pdgfrβ expressing cells enveloping CD31 expressing endothelial tubes in matrigel). Cell conversion graphs compare marker positivity in undifferentiated oCFU-Fs, differentiated oCFU-Fs and differentiated primary bone marrow CFU-Fs. (B) Cell conversion graphs for direct in vitro differentiation of oCFU-Fs into an endodermal derivative; hepatocytes (albumin and hepatocyte nuclear factor 4 alpha (Hnf-4a)). (C) Cell conversion graphs for direct in vitro differentiation of oCFU-Fs into neuro-ectodermal derivatives; neurons (neuron specific class III β-tubulin (Tuj1)), astrocytes (glial fibrillary acidic protein (Gfap)) and Oligodendrocytes (O4).

To interrogate qualitative differences between primary bone marrow stromal cells and reprogrammed osteocytes, micro, small and large colonies generated from GFP$^+$ stromal CFU-F and reprogrammed osteoblast oCFU-Fs shown in FIG. 2C, were serially passaged to evaluate their growth potential (FIG. 2E). Micro colonies from primary CFU-Fs could not be serially passaged and small colonies waned after a few passages. Continuous culture was possible only for the large colonies. In contrast, irrespective of size, all colonies generated by oCFU-Fs at the first passage had the intrinsic capacity to self renew. This suggested that within the micro and small colonies generated from oCFU-Fs, resided cells that had not yet gained their full growth potential. To systematically evaluate this, the inventors performed serial replatings of single cells from individual colonies (FIG. 2F). In accordance with the above observations, micro colonies generated by primary bone marrow stromal cells could not be propagated whereas cells within large colonies retained their heterogenous colony forming potential through serial passages. In contrast, first and second-generation micro-colonies generated by reprogrammed osteocytes, formed colonies that could propagate but with serial passages, this capacity was lost. Taken together, these findings suggested that the process of reprogramming was initiated by PDGF-AB/AZA treatment in some cells and continued to evolve through successive generations before stabilizing. Cell cycle analysis of pre- and post-treatment osteocytes showed that the proportion of cells in G2/M had increased (data not shown).

oCFU-Fs derived from reprogrammed primary osteocytes and primary bone marrow CFU-Fs, exhibited equivalent in vitro multipotency for a range of mesodermal lineages (endothelial cells, cardiomyocytes, smooth muscle cells, bone, cartilage and adipocytes) (FIG. 3A). In addition to displaying multiple lineage markers, in vitro differentiated cardiomyocytes showed spontaneous rhythmic contractility ~4.5 beats/sec (FIG. 3A) and in vitro differentiated endothelial cells showed ac-LDL (acetylated-Low Density Lipoprotein) uptake and formed tube like structures in matrigel. Indeed, oCFU-Fs generated endothelial tubes enveloped in pericytes in contrast to naked endothelial tubes formed by primary CFU-Fs (FIG. 3). To evaluate the trans-germ layer differentiation potential of oCFU-Fs, cells were differentiated in vitro into endodermal (hepatic) (FIG. 3B) and neuroectodermal (neuronal, astrocyte and oligodendrocyte) fates (FIG. 3C). However, oCFU-Fs did not form teratomas when transplanted under the kidney capsule and cannot be considered pluripotent by this criterion. Although early passage oCFU-Fs expressed pluripotency genes Oct4, cMyc, Nanog, Klf4, Sox2 and Rex1, their, levels were substantially lower than in ESCs. Primary osteoblasts did not express any of these genes whereas primary early passage bone marrow CFU-Fs whilst not expressing Klf4, Sox2 or Rex1 did express cMyc at levels that were equivalent to, and Oct4 and Nanog levels that were less than, those in oCFU-Fs (data not shown). Although lacking teratoma potential, oCFU-F cells (ubiquitously expressing cytoplasmic GFP) persisted in teratomas formed by co-transplantation with ESCs testifying to their in vivo plasticity. Mononuclear oCFU-F derivatives, detected with anti-GFP antibody or GFP fluorescence were seen in a range of mesodermal, ectodermal, neuro-ectodermal and endodermal lineages (data not shown). Taken together, these data show that primary osteocytes can be reprogrammed into MSC-like cells by transient exposure to PDGF-AB and AZA.

Figure 4:
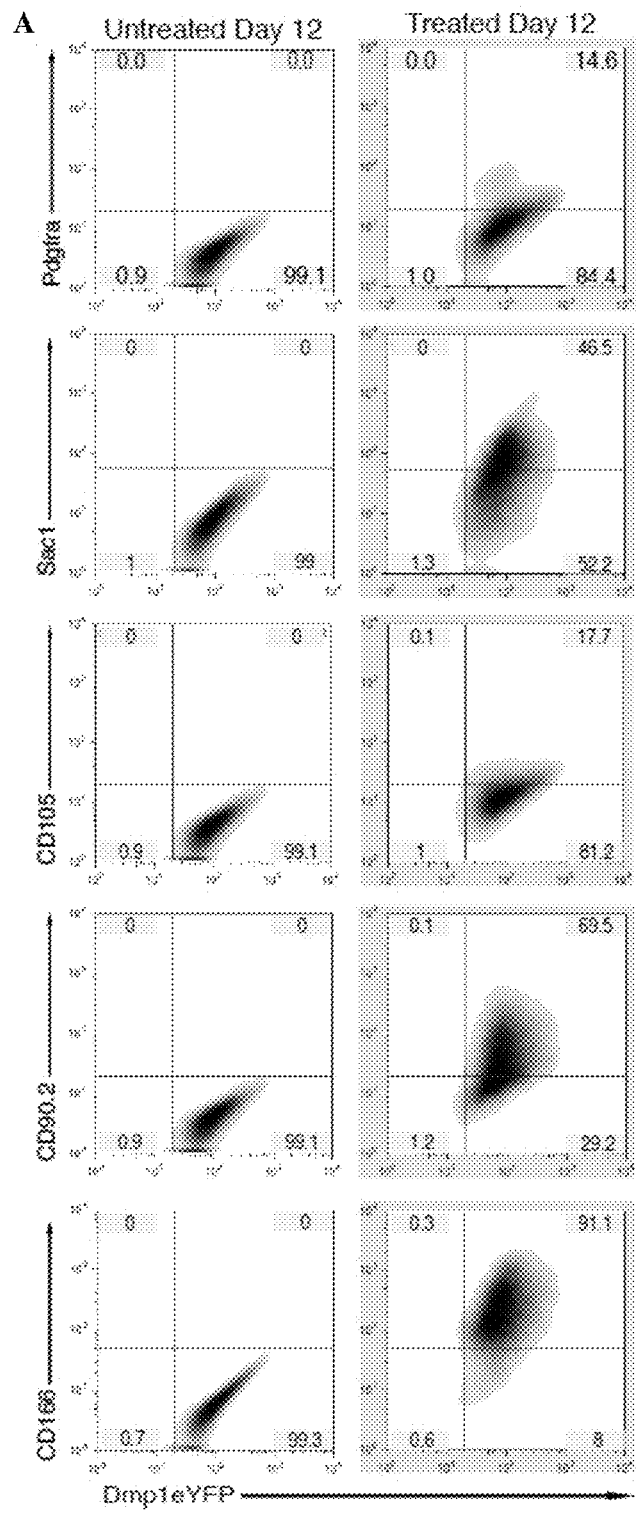
FIG. 4: PDGF-AB in combination with AZA reprograms Dmp1-eYFP osteocytes into MSC-like cells. (A) Flowcytometry of primary Dmp1-eYFP osteocytes maintained in media for 12 days with and without PDGF-AB/AZA. (B) Number and size distribution of plastic adherent colonies. CFU-F; primary bone marrow stromal cells, OC; osteocytes.
Figure 4:
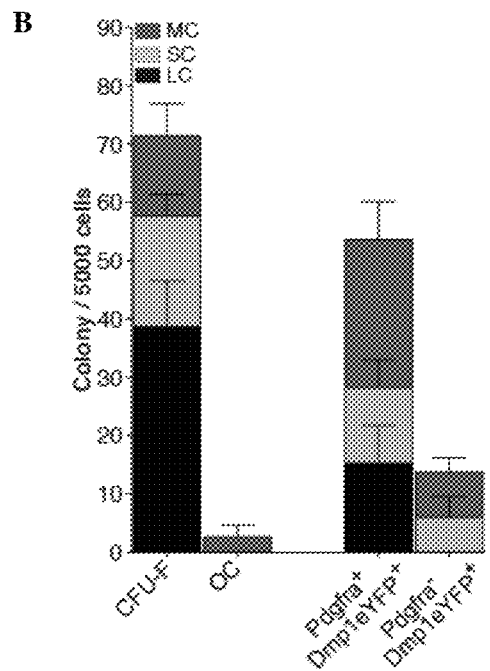

Example 3. PDGF-AB in Combination with AZA Reprograms Dmp1-eYFP Osteocytes into MSC-Like Cells Dense matrix protein 1 (Dmp1) marks terminally differentiated osteocytes. The inventors crossed Dmp1-cre transgenic mice with R26R-eYFP mice to generate transgenics with eYFP labelled osteocytes to investigate whether terminally differentiated cells (i.e. osteocytes) could be reprogrammed into MSC-like cells as efficiently as lineage committed progenitors (i.e. osteoblasts). Bones were flushed, fragmented, collagenase treated and cultured for a week. From cells that emanated from bone, Sca1$^-$/CD31$^-$/Pdgfr$\square^-$/eYFP$^+$ cells were sorted and either continuously live imaged in PDGF-AB/AZA supplemented MSC medium or maintained in MSC medium with or without PDGF-AB/AZA supplements for flowcytometry and CFU-F assays at day 12. The morphology of osteocytes changed from cells with a globular soma and fine branching cytoplasmic extensions, to flat elongated stromal cells (data not shown). In contrast to untreated cells, treated eYFP+ve osteocytes acquired MSC markers at day 12 albeit at varying frequency (FIG. 4A). A fraction of Dmp1-eYFP osteocytes (~15%) treated with PDGF-AB/AZA acquired Pdgfrα. The Pdgfrα+ve and −ve fractions were sorted and their CFU-F capacities, were assessed and compared with that of primary bone marrow stromal cells (CFU-F) and untreated osteocytes (OC) which had been maintained in media without PDGF-AB/AZA (FIG. 4B). Whereas untreated osteocytes could not form CFU-Fs, treated osteocytes that acquired surface Pdgfrα also acquired CFU-F potential.

Figure 5:
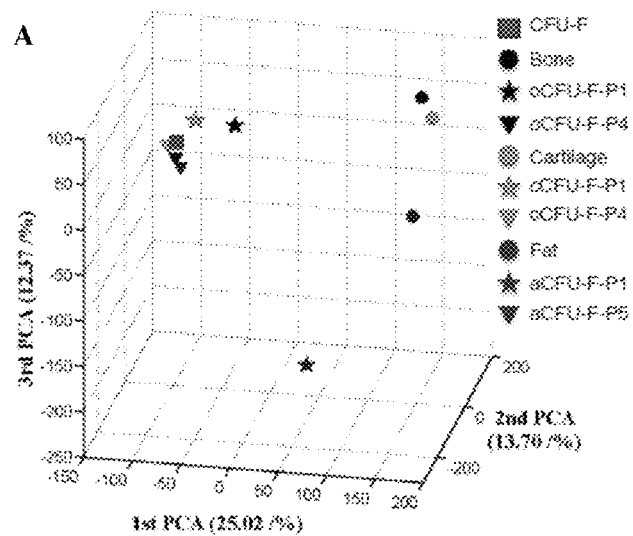
FIG. 5: Functional reprogramming of lineage committed cells into MSC-like cells is accompanied by progressive alteration of the molecular landscape. (A) Principal component analysis showing the spatial relationship between individual transcriptomes and later passages of oCFU-Fs, cCFU-Fs and aCFU-Fs. (B) CpG methylation at the Oct4 and Nanog promoters are shown for primary osteoblasts and oCFU-Fs. GpC sites are represented as circles and are shaded black when accessible and white when inaccessible to the DNA methylase. (C) Colony forming potential of bone marrow CFU-Fs, primary osteoblasts and oCFU-Fs (primary osteoblasts treated with PDGF-AB/AZA) with and without inhibitors (AG1296; a Pdgfrα/β inhibitor, APA5; a monoclonal antibody that binds and interferes with Pdgfrα function, JAKi1 and JAK2i2; Jak inhibitors, STAT3iVS and STAT3iP; Stat3 inhibitors, JNKi1L; a Jnk inhibitor. (D) Colony type and number with dual inhibition of STAT3 and JNK signalling. CFU-F; colony forming unit-fibroblast, oCFU-F; PDGF-AB/AZA treated bone cells cultured in MSC medium, cCFU-F; PDGF-AB/AZA treated cartilage cells cultured in MSC medium, aCFU-F; PDGF-AB/AZA treated fat cells cultured in MSC medium.
Figure 5:
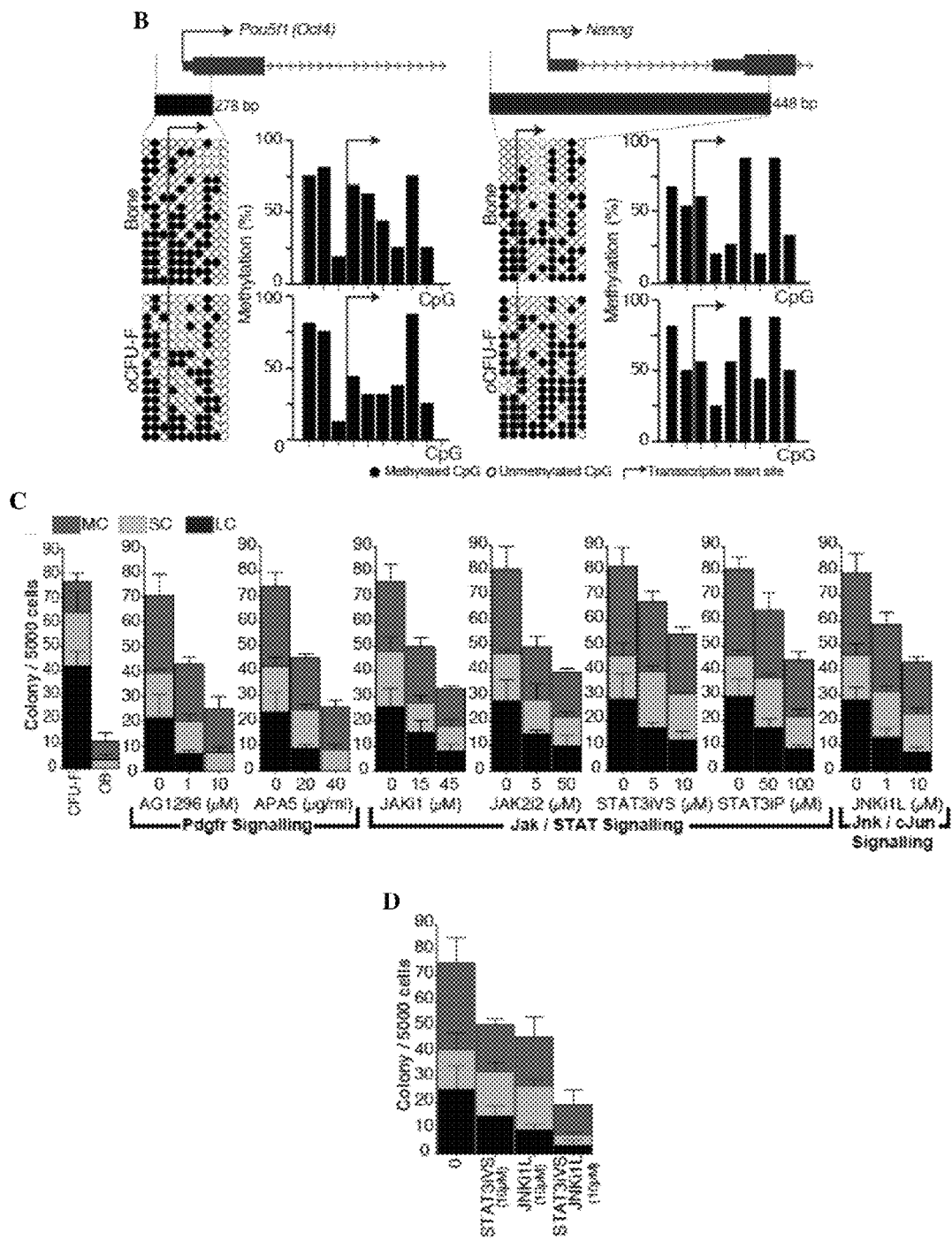

Example 4. Functional Reprogramming of Lineage-Committed Cells into MSC-Like Cells is Accompanied by Progressive Alteration of the Transcriptional Landscape To evaluate transcriptional changes that accompany cellular reprogramming by PDGF-AB/AZA, the inventors performed whole-genome expression analysis of in vitro differentiated bone, cartilage and fat cells before and after treatment with PDGF-AB/AZA. As expected the gene expression profiles of pre-treatment bone, cartilage and fat cells had sets of genes that were divergently expressed from those in primary undifferentiated bone marrow CFU-Fs (data not shown). Following 12 days of treatment, these divergently expressed genes converged and overlapped with expression profiles of primary undifferentiated CFU-Fs (data not shown). Gene set enrichment analyses (GSEA) showed that mitosis and stem cell related gene sets were enriched in bone marrow CFU-Fs relative to in vitro differentiated bone, whereas the gene set related to bone remodeling was enriched in bone cells. Expression profiles in reprogrammed bone cells (oCFU-Fs) were analysed relative to expression profiles in in vitro differentiated bone. Mitosis and stem cell gene sets were enriched and bone remodeling gene sets were depleted in oCFU-Fs relative to bone cells. Hierarchical clustering of these gene expression profiles showed that irrespective of the starting cell type, reprogrammed cells shared profiles that were most closely related to each other and clustered with primary CFU-Fs (data not shown). Principal component analysis (PCA) of expression profiles of pre- and post-treatment bone, cartilage and fat cells at P1 and P4/5 showed that the transcriptional convergence towards the CFU-F transcriptome was progressive (FIG. 5A).

Nucleosome occupancy and DNA methylation at gene promoters is associated with gene silencing (Jones, 2012). Gene re-expression on the other hand is associated with nucleosome eviction and DNA demethylation. To evaluate the dynamics of nucleosome positioning and DNA methylation during in vitro differentiation of BM-CFU-Fs into bone, cartilage and fat and their subsequent reprogramming into MSC-like cells, the inventors performed nucleosome occupancy and methylome sequencing (NOMe-seq), a method that permits assessment of both the nucleosome footprint and DNA methylation on the same DNA strand. Runx2 expression is associated with commitment to the osteogenic lineage (Karsenty, 2008) and is transcribed from a promoter that is devoid of CpGs. Runx2 promoter alleles were mostly free of nucleosomes in bone and fat cells but nucleosome dense in cartilage and PDGF-AB/AZA treatment evicted nucleosomes from the Runx2 promoter in all cell types (data not shown). Given the re-expression of pluripotency genes in lineage committed cells following PDGF-AB/AZA treatment, the inventors also performed bisulphite sequencing on primary osteoblasts before and after treatment to assess DNA methylation profiles at the promoters of Oct4, Nanog, Sox2, Klf4 and c-Myc (FIG. 5B). The majority of Oct4 alleles in osteoblasts show CpG methylation at their transcription start sites (FIG. 5B top row). There is marked reduction of methylation following PDGF-AB/AZA treatment (FIG. 5B bottom row). Interestingly less than half the Nanog alleles and almost none of the Sox2, Klf4 and c-Myc alleles in osteoblasts show CpG methylation at their transcription start sites (FIG. 5B) and the lack of expression of these genes likely relate to the absence of upstream transcriptional drivers in these cells. Given the transcriptional connectivity of these pluripotent genes, Oct4 re-expression in oCFU-Fs by promoter demethylation may serve as the driver for re-expression of the others.

Active Pdgf isoforms stimulate cells by binding to and activating signalling by dimerization of two distinct, but structurally related, membrane bound receptor tyrosine kinases; Pdgf receptor-α (Pdgfrα) and Pdgf receptor-β (Pdgfrβ). Pdgf-BB has a greater binding affinity for Pdgfrβ but can also bind Pdgfrα whereas Pdgf-AA interacts only with Pdgfrα. Therefore, Pdgf-AA induces αα-receptor homodimers, PDGF-AB, both αα-receptor homodimers and αβ-receptor heterodimers and Pdgf-BB, all three dimeric combinations of α and β receptors, however in vivo binding of PDGF-AB is not known. Primary osteoblasts express Pdgfrβ but not Pdgfrα. However, within 48 hours of exposure to AZA, Pdgfrα protein expression was evident on the surface of primary osteoblasts. Interestingly PDGF-AB alone also induced Pdgfrα expression albeit to a lesser extent. The combination of PDGF-AB and AZA induced more robust expression of surface Pdgfrα and concomitant reduction in surface Pdgfrβ expression on primary osteoblasts. Ingenuity pathway analysis (IPA) comparing expression levels of various mediators of Pdgfr signaling between bone cells and CFU-Fs showed differential expression which was reversed when oCFU-Fs were compared to bone (data not shown). These included expression of Pdgf receptors α and β, and components of the Jak/Stat and Jnk/c-Jun pathways but not the PI3kinase pathway. Inhibition of Pdgf receptors α and β using a non-selective inhibitor, AG1296 abolished PDGF-AB/AZA mediated oCFU-F production from primary osteoblasts (FIG. 5C). APA5, a selective monoclonal inhibitor that binds to and inactivates Pdgfrα also abolished oCFU-F production. There was also a dose dependent decrease in oCFU-F production when osteoblasts were reprogrammed in the presence of Jak/Stat3 and Jnk inhibitors (FIG. 5C). The combination of Stat3 and Jnk inhibitors was even more effective than either alone (FIG. 5D) but did not completely abolish large colony formation at the concentrations used. PI3kinase pathway inhibitors, Wortmannin and LY294002, on the other hand had no impact on oCFU-F production. pStat3, pJnk1 and pcJun protein levels were significantly elevated in osteoblasts 48 hours after exposure to PDGF-AB and AZA, and these increases were modulated by their respective inhibitors. Taken together these data suggest that Pdgfrα signaling is critical for PDGF-AB/AZA mediated reprogramming and that this is mediated in part by Jak/Stat3 and Jnk.

Figure 6:
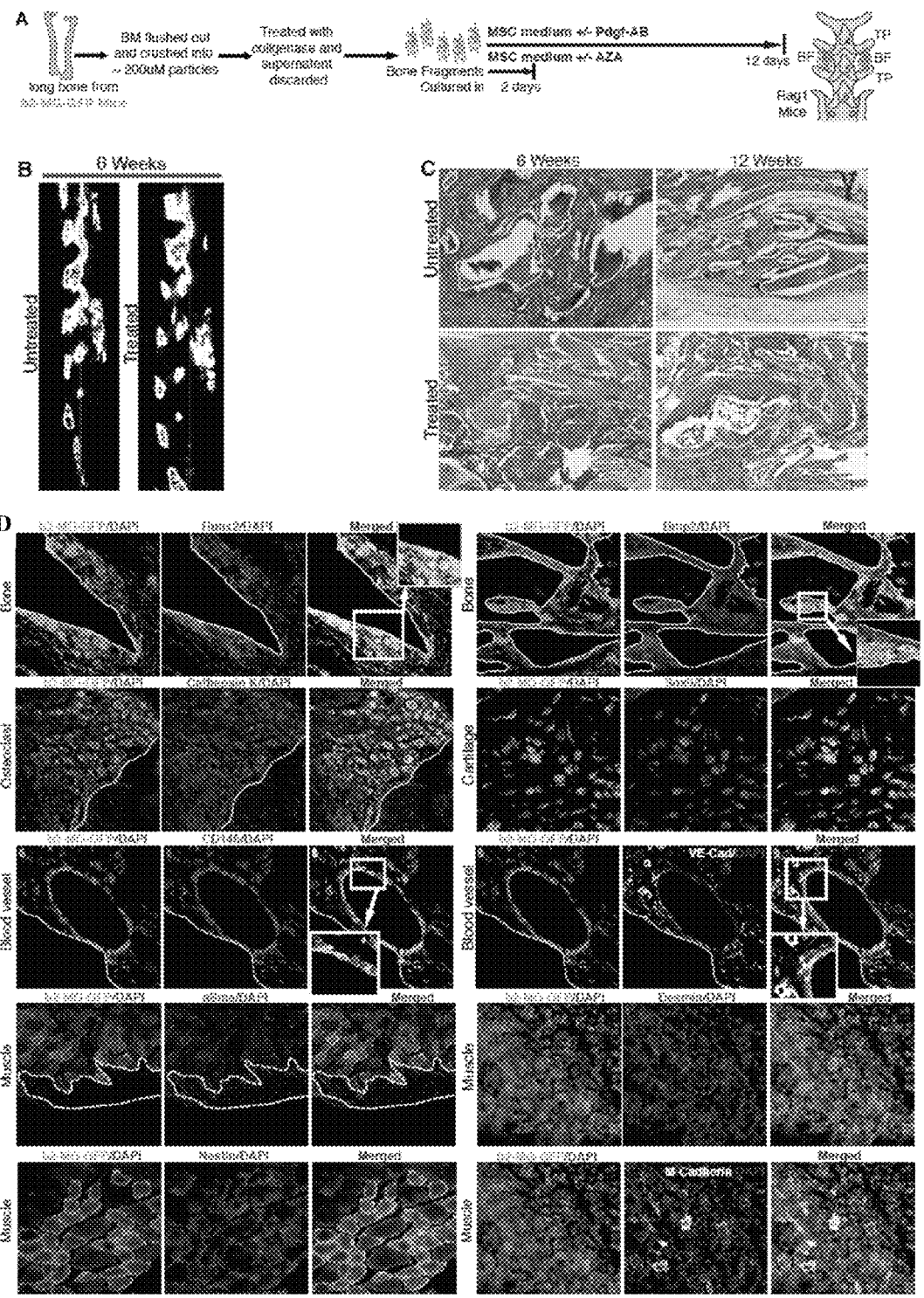
FIG. 6: oCFU-Fs contribute to tissue repair and regeneration in a lumbar spinal fusion mouse model. (A) A schematic representation of the experimental steps involved in harvesting bone from a ubiquitous GFP mouse (β2microglobulin-GFP), reprogramming in media with or without PDGF-AB/AZA (labeled as treated or untreated respectively) for 12 days and implanting dorso-laterally between the transverse processes of the lumbar spine. (B) Micro-CT images of mice implanted with untreated and treated bone fragments at 6 weeks. (C) Hematoxylin and Eosin stained sections of implanted fragments and surrounding tissues harvested at 6 and 12 weeks. Untreated bone fragments (top panels) showed no new bone generation whereas treated bone fragments (bottom panels) showed new woven bone with cartilage and marrow. (D) Confocal images of tissues surrounding treated bone fragments showing donor cell contribution to bone cells (Runx2 and Bmp2), osteoclasts (cathepsin-K), cartilage (Sox9), blood vessel (CD146 and VE-Cadherin) and skeletal muscle (aSMA, Desmin, Nestin and M-Cadherin).

Example 5. oCFU-Fs Contribute to Tissue Repair and Regeneration in a Lumbar Spinal Fusion Mouse Model To evaluate the potential for PDGF-AB and AZA to help regenerate and repair tissues in vivo, the inventors used a bilateral lumbar spinal fusion mouse model in which transverse processes of the lumbar vertebrae were decorticated and allogeneic bone fragments grafted into postero-lateral gutters to evaluate fusion with each other and host bone. Long bones were harvested from ubiquitous GFP mice (â2 microglobulin-GFP), flushed to evacuate bone marrow, fragmented and collagenase treated to denude surface adherent cells (FIG. 6A). The bone fragments were cultured in MSC medium alone or that supplemented with PDGF-AB/AZA for 12 days and transplanted into the postero-lateral gutters adjacent to the decorticated lumbar vertebrae. Bone fusion was evaluated using micro-CT and histology at 6 and 12-weeks. In the group transplanted with PDGF-AB/AZA treated fragments but not in those maintained in media alone, there was radiographic evidence of union between transplanted bone fragments themselves and with host bone evident both at 6 and 12 weeks (FIG. 6B). Tissues harvested from the graft site at 6 and 12-weeks showed new woven bone with marrow filled spaces adjacent to transplanted fragments (FIG. 6C). Treated but not untreated bone fragments (ubiquitous GFP) showed a rim of GFP$^+$ cells, some co-expressing the transient myoblast marker α-smooth muscle actin (aSma) and MSC marker vimentin extruding into the surrounding matrix (data not shown). Cells of the osteoblastic (Runx2, Bmp2), osteoclastic (Cathepsin-K), chondrocytic (Sox9), vascular (CD146$^+$ pericytes and VE-Cadherin$^+$ endothelial cells) lineages were readily identifiable adjacent to and were derived from transplanted PDGF-AB/AZA treated GFP$^+$ bone fragments at 6 and 12 weeks (FIG. 6D). In line with the radiographic evidence, there was no histological evidence of new bone or other tissue formation in sections of grafts harvested from mice transplanted with bone fragments cultured in MSC medium alone. During surgery, when decorticating the transverse processes and creating space to accommodate transplanted bone fragments, there is inevitable damage to surrounding skeletal muscle. It was striking to note that not only was there generation of new cancellous bone and associated tissues but histological evidence of transplant derived skeletal muscle fibers (FIG. 6D). There was no evidence of trans-germ layer differentiation or teratoma formation either at 6 or 12 weeks post-transplant. Taken together, these data show that cells from within PDGF-AB/AZA treated bone fragments, proliferate and contribute to tissue regeneration and repair in vivo.

Example 6. Functional Hierarchy of iMSC-LCs

Figure 7:
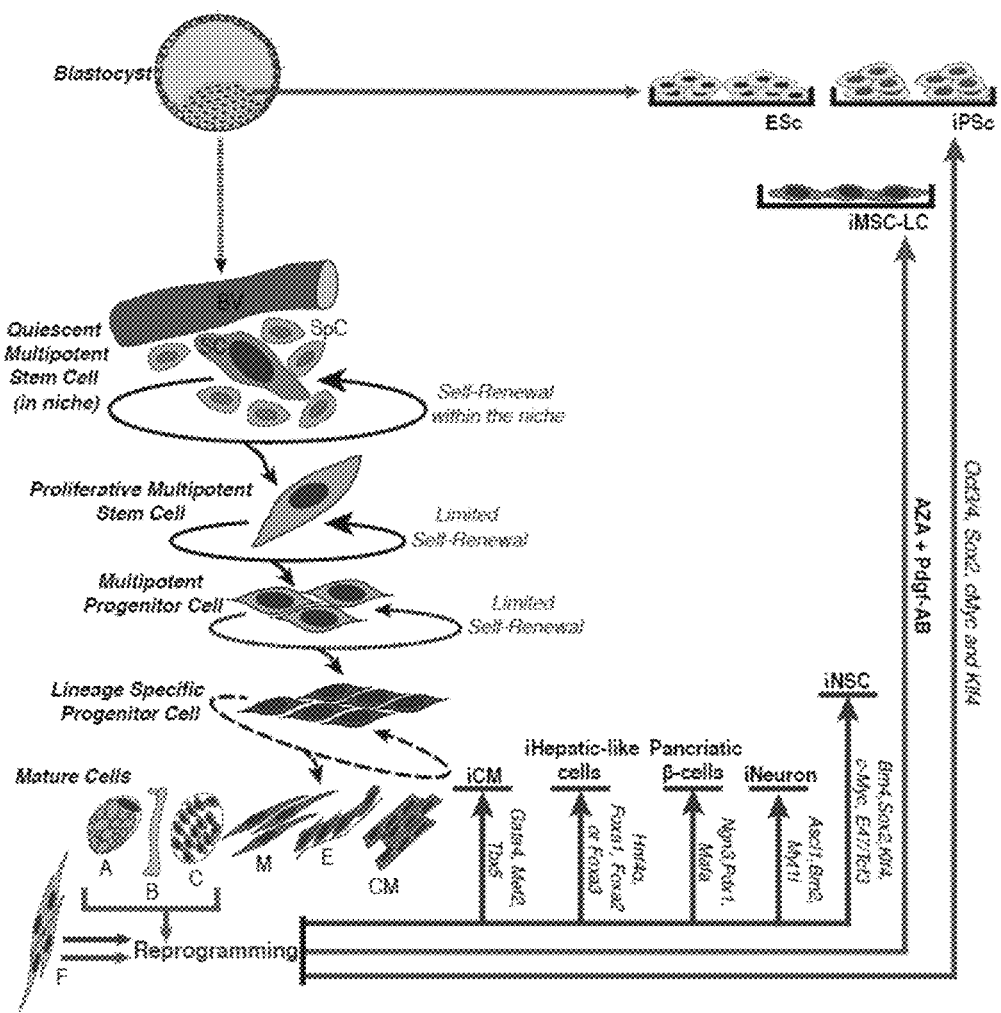
FIG. 7: Functional hierarchy of iMSC-LCs.

Functionally and immuno-phenotypically, iMSC-LCs resemble primary MSCs but there are molecular differences between these cells and MSCs as well as other tissue specific and pluripotent stem cells. Indeed primary MSCs expressed c-Myc, Oct4 and low levels of Nanog but iMSC-LCs expressed these as well as Sox2, Klf4 and Rex1 albeit at levels significantly lower than in ESCs. Although iMSC-LCs did not form teratomas, which ESCs do, the in vivo plasticity and tissue repair capability that these cells demonstrate may relate to the expression of these genes. Indeed, there was only partial DNA demethylation at the promoters of pluripotency genes suggesting that these loci are still ready to revert to an inactive state, which would be consistent with the ready differentiation of reprogrammed cells into somatic tissues. iMSC-LCs may not have a comparable normal counterpart but their functional and molecular characteristics would place them along a spectrum between MSCs and ES/iPS cells (FIG. 7). Whereas defined factors have previously been shown to reprogram fibroblasts into lineage specific progenitors and pluripotent stem cells, the combination of PDGF-AB and AZA reprograms differentiated cells into multipotent stem cells with broad in vivo tissue regenerative capacity.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or feature.

REFERENCES

Chong, J. J., et al. (2011). Adult cardiac-resident MSC-like stem cells with a proepicardial origin. Cell Stem Cell 9, 527-540.
Diffner, E., et al. (2013). Activity of a heptad of transcription factors is associated with stem cell programs and clinical outcome in acute myeloid leukemia. Blood 121, 2289-2300.
Hamilton, T. G., et al. (2003). Evolutionary divergence of platelet-derived growth factor alpha receptor signaling mechanisms. Mol Cell Biol 23, 4013-4025.
Hesson, L. B., et al. (2013). Reassembly of Nucleosomes at the MLH1 Promoter Initiates Resilencing Following Decitabine Exposure. PLoS Genet 9, e1003636.
Mombaerts, P. et al. (1992). Rag-1 deificiant mice have no mature B and T lymphocytes. Cell 68, 869-877.
Schaefer, B. C., et al. (2001). Observation of antigen-dependent CD8+ T-cell/dendritic cell interactions in vivo. Cell Immunol 214, 110-122.
Stem, A. R., et al. (2012). Isolation and culture of primary osteocytes from the long bones of skeletally mature and aged mice. BioTechniques 52, 361-373.

The invention claimed is:

1. A method of generating a mammalian multilineage potential cell, said method comprising contacting a mammalian somatic cell exhibiting a mature phenotype with a PDGF-AB dimer, wherein the A subunit of the dimer comprises the amino acid sequence of SEQ ID NO:1 and the B subunit of the dimer comprises the amino acid sequence of SEQ ID NO:2, and 5-azacytidine or 5-aza-2'-deoxycytidine for a time and under conditions sufficient to induce the transition of said somatic cell to a cell exhibiting multilineage differentiative potential.

2. A method according to claim 1, wherein the mammalian somatic cell exhibiting a mature phenotype is a mesenchyme-derived somatic cell.

3. A method according to claim 1, wherein the mammalian somatic cell exhibiting a mature phenotype is selected from a fibroblast, adipocyte, chondrocyte, osteoblast and osteocyte.

4. A method according to claim 1, wherein the somatic cell is contacted for a first period of time with the PDGF-AB dimer and 5-azacytidine or 5-aza-2'-deoxycytidine, and subsequently for a second period of time with the PDGF-AB dimer in the absence of the 5-azacytidine or 5-aza-2'-deoxycytidine.

5. A method according to claim 4, wherein the first period of time is between about 12 to 72 hours.

6. A method according to claim 4, wherein the second period of time is between about 7 to 12 days.

7. A method according to claim 1, further comprising the step of contacting the cell produced, exhibiting multilineage differentiative potential, with a stimulus to direct the differentiation of said cell to a mesenchymal phenotype.

8. A method for promoting or inducing tissue repair or regeneration, said method comprising
   contacting one or more mammalian somatic cells exhibiting a mature phenotype with a PDGF-AB dimer, wherein the A subunit of the dimer comprises the amino acid sequence of SEQ ID NO:1 and the B subunit of the dimer comprises the amino acid sequence of SEQ ID NO:2, and 5-azacytidine or 5-aza-2'-deoxycytidine for a time and under conditions sufficient to induce the transition of said somatic cells to cells exhibiting multilineage differentiative potential; and
   administering to a mammal in need thereof an effective number of said cells exhibiting multilineage differentiative potential.

9. A method according to claim 8, wherein the tissue is connective tissue.

10. A method according to claim 9, wherein the tissue is selected from bone, cartilage, smooth muscle, tendon, ligament, stroma, marrow, dermis and fat.

* * * * *

SEQUENCE LISTING

<160> NUMBER OF SEQ ID NOS: 34

<210> SEQ ID NO 1
<211> LENGTH: 211
<212> TYPE: PRT
<213> ORGANISM: Homo sapiens

<400> SEQUENCE: 1

Met Arg Thr Leu Ala Cys Leu Leu Leu Leu Gly Cys Gly Tyr Leu Ala
1               5                   10                  15

His Val Leu Ala Glu Glu Ala Glu Ile Pro Arg Glu Val Ile Glu Arg
            20                  25                  30

Leu Ala Arg Ser Gln Ile His Ser Ile Arg Asp Leu Gln Arg Leu Leu
        35                  40                  45

Glu Ile Asp Ser Val Gly Ser Glu Asp Ser Leu Asp Thr Ser Leu Arg
    50                  55                  60

Ala His Gly Val His Ala Thr Lys His Val Pro Glu Lys Arg Pro Leu
65                  70                  75                  80

Pro Ile Arg Arg Lys Arg Ser Ile Glu Glu Ala Val Pro Ala Val Cys
                85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Thr Ser Leu Asn Pro Asp Tyr Arg Glu Glu Asp
            180                 185                 190

Thr Gly Arg Pro Arg Glu Ser Gly Lys Lys Arg Lys Arg Lys Arg Leu
        195                 200                 205

Lys Pro Thr
    210

<210> SEQ ID NO 2
<211> LENGTH: 241
<212> TYPE: PRT
<213> ORGANISM: Homo sapiens

<400> SEQUENCE: 2

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

```
Cys Lys Thr Arg Thr Glu Val Phe Glu Ile Ser Arg Arg Leu Ile Asp
            100                 105                 110
Arg Thr Asn Ala Asn Phe Leu Val Trp Pro Pro Cys Val Glu Val Gln
        115                 120                 125
Arg Cys Ser Gly Cys Cys Asn Asn Arg Asn Val Gln Cys Arg Pro Thr
    130                 135                 140
Gln Val Gln Leu Arg Pro Val Gln Val Arg Lys Ile Glu Ile Val Arg
145                 150                 155                 160
Lys Lys Pro Ile Phe Lys Lys Ala Thr Val Thr Leu Glu Asp His Leu
                165                 170                 175
Ala Cys Lys Cys Glu Thr Val Ala Ala Ala Arg Pro Val Thr Arg Ser
            180                 185                 190
Pro Gly Gly Ser Gln Glu Gln Arg Ala Lys Thr Pro Gln Thr Arg Val
        195                 200                 205
Thr Ile Arg Thr Val Arg Val Arg Arg Pro Pro Lys Gly Lys His Arg
    210                 215                 220
Lys Phe Lys His Thr His Asp Lys Thr Ala Leu Lys Glu Thr Leu Gly
225                 230                 235                 240
Ala

<210> SEQ ID NO 3
<211> LENGTH: 23
<212> TYPE: DNA
<213> ORGANISM: Homo sapiens

<400> SEQUENCE: 3
tctttccacc aggcccccgg ctc                                           23

<210> SEQ ID NO 4
<211> LENGTH: 23
<212> TYPE: DNA
<213> ORGANISM: Homo sapiens

<400> SEQUENCE: 4
tgcgggcgga catggggaga tcc                                           23

<210> SEQ ID NO 5
<211> LENGTH: 21
<212> TYPE: DNA
<213> ORGANISM: Homo sapiens

<400> SEQUENCE: 5
aggacaggtt tcagaagcag a                                             21

<210> SEQ ID NO 6
<211> LENGTH: 23
<212> TYPE: DNA
<213> ORGANISM: Homo sapiens

<400> SEQUENCE: 6
ccattgctag tcttcaacca ctg                                           23

<210> SEQ ID NO 7
<211> LENGTH: 23
<212> TYPE: DNA
<213> ORGANISM: Homo sapiens

<400> SEQUENCE: 7
tagagctaga ctccgggcga tga                                           23
```

```
<210> SEQ ID NO 8
<211> LENGTH: 23
<212> TYPE: DNA
<213> ORGANISM: Homo sapiens

<400> SEQUENCE: 8
ttgccttaaa caagaccacg aaa                                             23

<210> SEQ ID NO 9
<211> LENGTH: 24
<212> TYPE: DNA
<213> ORGANISM: Homo sapiens

<400> SEQUENCE: 9
gcgaactcac acaggcgaga aacc                                            24

<210> SEQ ID NO 10
<211> LENGTH: 23
<212> TYPE: DNA
<213> ORGANISM: Homo sapiens

<400> SEQUENCE: 10
tcgcttcctc ttcctccgac aca                                             23

<210> SEQ ID NO 11
<211> LENGTH: 28
<212> TYPE: DNA
<213> ORGANISM: Homo sapiens

<400> SEQUENCE: 11
tgacctaact cgaggaggag ctggaatc                                        28

<210> SEQ ID NO 12
<211> LENGTH: 32
<212> TYPE: DNA
<213> ORGANISM: Homo sapiens

<400> SEQUENCE: 12
aagtttgagg cagttaaaat tatggctgaa gc                                   32

<210> SEQ ID NO 13
<211> LENGTH: 24
<212> TYPE: DNA
<213> ORGANISM: Homo sapiens

<400> SEQUENCE: 13
acgagtggca gtttcttctt ggga                                            24

<210> SEQ ID NO 14
<211> LENGTH: 24
<212> TYPE: DNA
<213> ORGANISM: Homo sapiens

<400> SEQUENCE: 14
tatgactcac ttccaggggg cact                                            24

<210> SEQ ID NO 15
<211> LENGTH: 21
<212> TYPE: DNA
<213> ORGANISM: Homo sapiens

<400> SEQUENCE: 15
cctaaggcca accgtgaaaa g                                               21
```

```
<210> SEQ ID NO 16
<211> LENGTH: 21
<212> TYPE: DNA
<213> ORGANISM: Homo sapiens

<400> SEQUENCE: 16
tcttcatggt gctaggagcc a                                          21

<210> SEQ ID NO 17
<211> LENGTH: 32
<212> TYPE: DNA
<213> ORGANISM: Homo sapiens

<400> SEQUENCE: 17
ttttgytttt tagaggytta attttatagg ag                              32

<210> SEQ ID NO 18
<211> LENGTH: 35
<212> TYPE: DNA
<213> ORGANISM: Homo sapiens

<400> SEQUENCE: 18
tattcctrca taaactataa ttaaarcact cacta                           35

<210> SEQ ID NO 19
<211> LENGTH: 33
<212> TYPE: DNA
<213> ORGANISM: Homo sapiens

<400> SEQUENCE: 19
ctaaaaaaaa tttrcaccrc acttataatt cta                             33

<210> SEQ ID NO 20
<211> LENGTH: 31
<212> TYPE: DNA
<213> ORGANISM: Homo sapiens

<400> SEQUENCE: 20
gaygttttta attttygttt ggaagatata g                               31

<210> SEQ ID NO 21
<211> LENGTH: 28
<212> TYPE: DNA
<213> ORGANISM: Homo sapiens

<400> SEQUENCE: 21
yaacataaaa aaatccccaa tacctcta                                   28

<210> SEQ ID NO 22
<211> LENGTH: 31
<212> TYPE: DNA
<213> ORGANISM: Homo sapiens

<400> SEQUENCE: 22
gtttatggtg gattttgyag gtgggattaa t                               31

<210> SEQ ID NO 23
<211> LENGTH: 32
<212> TYPE: DNA
<213> ORGANISM: Homo sapiens

<400> SEQUENCE: 23
tcttcraaaa ctaaattcct taccarcctc ta                              32
```

<210> SEQ ID NO 24
<211> LENGTH: 29
<212> TYPE: DNA
<213> ORGANISM: Homo sapiens

<400> SEQUENCE: 24
cttaccarcc tctatrcaaa rcatctcaa                                    29

<210> SEQ ID NO 25
<211> LENGTH: 30
<212> TYPE: DNA
<213> ORGANISM: Homo sapiens

<400> SEQUENCE: 25
ygyggagttt gtttatttag ttattatggt                                   30

<210> SEQ ID NO 26
<211> LENGTH: 29
<212> TYPE: DNA
<213> ORGANISM: Homo sapiens

<400> SEQUENCE: 26
crcraaatac raaatcctaa aaactatac                                    29

<210> SEQ ID NO 27
<211> LENGTH: 35
<212> TYPE: DNA
<213> ORGANISM: Homo sapiens

<400> SEQUENCE: 27
gygttttatt tatttttatg tatttaagag agagt                             35

<210> SEQ ID NO 28
<211> LENGTH: 34
<212> TYPE: DNA
<213> ORGANISM: Homo sapiens

<400> SEQUENCE: 28
aataaacaac catccatata ataaaaacta tcaa                              34

<210> SEQ ID NO 29
<211> LENGTH: 26
<212> TYPE: DNA
<213> ORGANISM: Homo sapiens

<400> SEQUENCE: 29
agaagtttgg agttygaggt ttaagt                                       26

<210> SEQ ID NO 30
<211> LENGTH: 30
<212> TYPE: DNA
<213> ORGANISM: Homo sapiens

<400> SEQUENCE: 30
ttcaactccr tctccatcat attatacata                                   30

<210> SEQ ID NO 31
<211> LENGTH: 30
<212> TYPE: DNA
<213> ORGANISM: Homo sapiens

<400> SEQUENCE: 31
gaataatygt atagaaaggg aaaggattag                                   30

```
<210> SEQ ID NO 32
<211> LENGTH: 29
<212> TYPE: DNA
<213> ORGANISM: Homo sapiens

<400> SEQUENCE: 32
craaaaactt cttttatact acractcaa                                          29

<210> SEQ ID NO 33
<211> LENGTH: 24
<212> TYPE: DNA
<213> ORGANISM: Homo sapiens

<400> SEQUENCE: 33
ttggaagagt ygtgtgtgta gagt                                               24

<210> SEQ ID NO 34
<211> LENGTH: 33
<212> TYPE: DNA
<213> ORGANISM: Homo sapiens

<400> SEQUENCE: 34
caactcraaa aactcttttc aaaaaaacta atc                                     33
```